United States Patent [19]
Warren et al.

[11] Patent Number: 5,118,792
[45] Date of Patent: Jun. 2, 1992

[54] ICE CRYSTAL GROWTH SUPPRESSION POLYPEPTIDES AND METHOD OF MAKING

[75] Inventors: Gareth J. Warren; Gunhild M. Mueller, both of San Francisco; Robert L. McKown, Albany, all of Calif.

[73] Assignee: DNA Plant Technology Corporation, Oakland, Calif.

[21] Appl. No.: 350,481

[22] Filed: May 10, 1989

[51] Int. Cl.⁵ .................... C12P 21/02; C07K 13/00
[52] U.S. Cl. .................................. 530/350; 426/321; 426/656; 426/657; 435/69.1; 435/69.7
[58] Field of Search .................. 435/68.1, 69.1, 69.7; 530/350; 514/773, 971; 426/321, 327, 524, 656, 657

[56] References Cited
PUBLICATIONS

Davies, P. L., Roach, A. H., Hew, G. L. (1982) Proc. Natl. Acad. Sci. U.S.A., 79, 335–339.
Pickett, M., Scott, G., Davies, P., Wang, N., Joshi, S., & Hew, C. (1984) *Eur. J. Biochem.*, 143, 35–38.
Chou, P. Y. & Fasman, G. D. (1974) *Biochemistry*, 13, 222–245.

*Primary Examiner*—Douglas W. Robinson
*Assistant Examiner*—Jon P. Weber
*Attorney, Agent, or Firm*—Townsend and Townsend

[57] ABSTRACT

Novel methods of improving freezing tolerance of organic materials through the use of antifreeze polypeptides is provided. These polypeptides increase the storage life of foodstuffs and biologics, as well as protect plant products, such as during growth. The antifreeze polypeptides, or their fusion proteins, may be produced chemically or by recombinant DNA techniques, and then purified for a variety of uses.

7 Claims, 29 Drawing Sheets

SYMBOLS FOR AMINO ACIDS

| | | |
|---|---|---|
| A | ALA | ALANINE |
| B | ASX | ASPARAGINE OR ASPARTIC ACID |
| C | CYS | CYSTEINE |
| D | ASP | ASPARTIC ACID |
| E | GLU | GLUTAMIC ACID |
| F | PHE | PHENYLALANINE |
| G | GLY | GLYCINE |
| H | HIS | HISTIDINE |
| I | IIE | ISOLEUCINE |
| K | LYS | LYSINE |
| L | LEU | LEUCINE |
| M | MET | METHIONINE |
| N | ASN | ASPARAGINE |
| P | PRO | PROLINE |
| Q | GLN | GLUTAMINE |
| R | ARG | ARGININE |
| S | SER | SERINE |
| T | THR | THREONINE |
| V | VAL | VALINE |
| W | TRP | TRYPTOPHAN |
| Y | TYR | TYROSINE |
| Z | GLX | GLUTAMINE OR GLUTAMIC ACID |

FIG._1.

| | | |
|---|---|---|
| TYPE 1 | DTASD | AAAAAA |
| TYPE 2 | LTAAN | AKAAAE |
| TYPE 3 | LTAAN | AAAAAA |
| TYPE 4 | LTAAN | AAAAAK |
| TYPE 5 | LTADN | AAAAAA |
| TYPE 6 | ATAAT | AAAAAA |
| TYPE 7 | ATAAT | AAKAAA |
| CONSENSUS | lTAon | AaaAAa |

FIG._2.

| | | | | | | |
|---|---|---|---|---|---|---|
| Saf 3 | MAA - | TYPE 1 - | TYPE 3 - | TYPE 3 - | ATAA | |
| Saf 4 | MAA - | TYPE 1 - | TYPE 3 - | TYPE 3 - | TYPE 3 - | ATAA |
| Saf 5 | MAA - | TYPE 1 - | TYPE 3 - | TYPE 3 - | TYPE 3 - | TYPE 3 - ATAA |
| Saf 6 | M - | TYPE 1 - | TYPE 3 - | TYPE 3 - | ATAA | |
| Saf 7 | M - | TYPE 1 - | TYPE 3 - | TYPE 3 - | TYPE 3 - | ATAA |
| Saf 8 | M - | TYPE 1 - | TYPE 3 - | TYPE 3 - | ATAR | |
| Saf 9 | M - | TYPE 1 - | TYPE 3 - | TYPE 3 - | TYPE 3 - | ATAR |
| Saf 10 | M - | TYPE 1 - | TYPE 4 - | TYPE 5 - | ATAR | |

FIG._3.

```
SS8-1           NGETP AQKAAR      IST
                LAAAA ALAAKT
                AADAA AKAAAK
                AAAIA AAAASA

SS3             MNAPA RAAAKT      IST
                AADAL AAAKKT
                AADAA AAAAAA
```

FIG._4.

| FUSION TO (PROTEIN) | ADVANTAGES OF FUSION |
|---|---|
| PROTEIN A | DETECTABILITY, SECRETION FROM GRAM-POSITIVE BACTERIA, PURIFICATION, READILY CLEAVED TO YIELD FREE PEPTIDE. |
| BETA-GALACTOSIDASE | MEASUREMENT BY ENZYME ASSAY, DETECTABILITY ON WESTERN BLOTS |
| BETA-LACTAMASE | DETECTABILITY ON WESTERN BLOTS, SECRETION TO PERIPLASM IN GRAM-NEGATIVE BACTERIA. |
| CHLORAMPHENICOL ACETYLTRANSFERASE | DETECTABILITY ON WESTERN BLOTS, MEASUREMENT BY ENZYME ASSAY IN PLANT EXTRACTS. |
| PATHOGENESIS-RELATED PROTEIN PR1B | SECRETION FROM DICOTYLEDONOUS PLANTS. |
| ALPHA-AMYLASE | SECRETION FROM MONOCOTYLEDONOUS PLANTS. |
| PHYTOHEMAGGLUTININ | VACUOLE TARGETING IN PLANTS. |
| RuBPCASE SMALL SUBUNIT | CHLOROPLAST TARGETING IN PLANTS. |
| PHASEOLIN | ACCUMULATION IN SEEDS. |
| ALCOHOL DEHYDROGENASE | EXPRESSION IN YEAST. |
| ALPHA MATING FACTOR | SECRETION FROM YEAST. |
| LUCIFERASE | DETECTABILITY BY LIGHT EMISSION. |

FIG._5.

DS OLIGO 1

```
5'    CCGGGCCATG GCTGCAGACA CTGCTAGCGA TGCCGCCGC GGCAGCAGC
3'       CGGTAC CGACGTCTGT GACGATCGCT ACGGCGGCG CCGTCGTCG

AGCAACTGCA GCATAAGCTT GCA -3'
      TCGTTGACGT CGTATTCGA      -5'
```

DS OLIGO 2

```
5'      CGCCGC CGCGGCCGCT GCTTTGACAG CTGCTAACG CCGCCGCGGCTGCA
3' CATGGCGGCG GCGCCGGCGA CGAAACTGTC GACGATTGC GGCGGCGCCG      5'
```

DS OLIGO 3

```
5'    GGCCGCTG CTTTGACAGC TGCTAACGCC GCCGC 3'
3' CGCCGGCGAC GAAACTGTCG ACGATTGCGG CGG    5'
```

DS OLIGO 4

```
5' CCGGGTACCA TGGACACTG        3'
3'       CATGGT ACCTGTGACGATC 5'
```

DS OLIGO 5

```
5'    CGTTAA CAACATCCGG ATCCA        3'
3' ACGTGCAATT GTTGTAGGCC TAGGTTCGA 5'
```

FIG._6A.

DS OLIGO 6

```
5'  GGCCGCTAAA CTGACTGCAG ATAATGCTGC CGC 3'
3'       CGATTT GACTGACGTC TATTACGACG G   5'
```

---

DS OLIGO 7

```
5'  AATTCCATGG TCGACAAGCG TTAACTCGAG GATTAAGGAT CCTGCAGAT
         GGTACC AGCTGTTCGC AATTGAGCTC CTAATTCCTA GGACGTCTA

ATCGAT 3'
    TAGCTATCGA 5'
```

---

DS OLIGO 8

```
5'  AATTCCCGGG TCGACATTGA AGGTCGCGAC ACTG       3'
3'       GGGCCC AGCTGTAACT TCCAGCGCTG TGACGATC 5'
```

ANTIFREEZE GENE Saf3 AS CLONED IN pUC118 (CONSTRUCT IS pLVC83)

```
                              M   A   A   D
gaattcgagctcggt acc cgg gcc ATG GCT GCA GAC
EcoRI—      KpnI—       NcoI—
    SstI—      XmaI—            PstI—
```

```
 T   A   S   D   A   A   A   A   A   A   L
ACT GCT AGC GAT GCC GCC GCG GCC GCT GCT TTG
    NheI—           SacII—
                         NotI—
             BglI—
```

```
 T   A   A   N   A   A   A   A   A   A   L
ACA GCT GCT AAC GCC GCC GCG GCC GCT GCT TTG
 PvuII—             BacII—
                         NotI—
             BglI—
```

```
 T   A   A   N   A   A   A   A   A   A   A
ACA GCT GCT AAC GCC GCC GCG GCA GCA GCA GCA
 PvuII—              SacII—
             BglI—
```

```
 T   A   A   ***
ACT GCA GCA TAA gcttgcaggcatgcaagctt
 PstI—      Hind3—           Hind3—
                    SphI—
```

---

ANTIFREEZE GENE Saf3 AS CLONED IN pUC119 (pGMM1)

```
                              M   A   A   L
gaattcgagctcggt acc cgg gcc ATG GCT GCA GAC
EcoRI—      KpnI—       NcoI—
    SstI—      XmaI—            PstI—
```

```
 T   A   S   D   A   A   A   A   A   A   L
ACT GCT AGC GAT GCC GCC GCG GCC GCT GCT TTG
    NheI—           SacII—
                         NotI—
             BglI—
```

```
 T   A   A   N   A   A   A   A   A   A   L
ACA GCT GCT AAC GCC GCC GCG GCC GCT GCT TTG
 PvuII—             SacII—
                         NotI—
             BglI—
```

```
 T   A   A   N   A   A   A   A   A   A   A
ACA GCT GCT AAC GCC GCC GCG GCA GCA GCA GCA
 PvuII—              SacII—
             BglI—
```

```
 T   A   A   ***
ACT GCA GCA TAA gctt
 PstI—      Hind3—
```

FIG._6C.

ANTIFREEZE GENE Saf4, AS CLONED IN pUCII9 (CONSTRUCT IS pLVC85)

```
                              M   A   A   D
gaattcgagctcggt acc cgg gcc ATG GCT GCA GAC
EcoRI-         KpnI—        NcoI——
    SstI—         KmaI—              PstI——

T   A   S   D   A   A   A   A   A   A   L
ACT GCT AGC GAT GCC GCC GCG GCC GCT GCT TTG
    NheI—            SacII—
                        NotI——
            BglI—————

T   A   A   N   A   A   A   A   A   A   L
ACA GCT GCT AAC GCC GCC GCG GCC GCT GCT TTG
 PvuII—              SacII—
                        NotI——
            BglI—————

T   A   A   N   A   A   A   A   A   A   L
ACA GCT GCT AAC GCC GCC GCG GCC GCT GCT TTG
 PvuII—              SacII—
                        NotI——
            BglI—————

T   A   A   N   A   A   A   A   A   A   A
ACA GCT GCT AAC GCC GCC GCG GCA GCA GCA GCA
 PvuII—              SacII—
            BglI—————

T   A   A   ***
ACT GCA GCA TAA gctt
 PstI——      Hind3—
```

FIG._6D.

```
ANTIFREEZE GENE Saf3, AS CLONED IN pBR322 (CONSTRUCT IS pLVC84)
                                    A   D
                                 CT GCA GAC
                                 PstI——

T   A   S   D   A   A   A   A   A   A   L
ACT GCT AGC GAT GCC GCC GCG GCC GCT GCT TTG
    NheI—           SacII—
                       NotI——
           BglI——

T   A   A   N   A   A   A   A   A   A   L
ACA GCT GCT AAC GCC GCC GCG GCC GCT GCT TTG
    PvuII—          SacII—
                       NotI——
           BglI——

T   A   A   N   A   A   A   A   A   A   A
ACA GCT GCT AAC GCC GCC GCG GCA GCA GCA GCA
    PvuII—          SacII—
           BglI——

T   A
ACT GCA G
PstI——
```

```
ANTIFREEZE GENE Saf3, AS CLONED IN pRIT5 (CONSTRUCT IS pGMM2)
                         M   A   A   D
   gaattcc cgg gcc  ATG GCT GCA GAC
   EcoRI-       NcoI——
         XmaI——            PstI——

T   A   S   D   A   A   A   A   A   A   L
ACT GCT AGC GAT GCC GCC GCG GCC GCT GCT TTG
    NheI—           SacII—
                       NotI——
           BglI——

T   A   A   N   A   A   A   A   A   A   L
ACA GCT GCT AAC GCC GCC GCG GCC GCT GCT TTG
    PvuII—          SacII—
                       NotI——
           BglI——

T   A   A   N   A   A   A   A   A   A   A
ACA GCT GCT AAC GCC GCC GCG GCA GCA GCA GCA
    PvuII—          SacII—
           BglI——

T   A   A   ***
ACT GCA GCA TAA gctt
PstI——      Hind3-
```

FIG._6E.

ANTIFREEZE GENE Saf4, AS CLONED IN pRIT5 (pRLM104)

```
                              M   A   A   D
         gaattcc cgg gcc ATG GCT GCA GAC
         EcoRI-      NcoI——
             XmaI——            PstI——

T   A   S   D   A   A   A   A   A   A   L
ACT GCT AGC GAT GCC GCC GCG GCC GCT GCT TTG
    NheI—          SacII——
                   NotI——
         BglI——————————

T   A   A   N   A   A   A   A   A   A   L
ACA GCT GCT AAC GCC GCC GCG GCC GCT GCT TTG
PvuII—             SacII——
                   NotI——
         BglI——————————

T   A   A   N   A   A   A   A   A   A   L
ACA GCT GCT AAC GCC GCC GCG GCC GCT GCT TTG
PvuII—             SacII——
                   NotI——
         BglI——————————

T   A   A   N   A   A   A   A   A   A   A
ACA GCT GCT AAC GCC GCC GCG GCA GCA GCA GCA
PvuII—             SacII——
         BglI——————————

T   A   A  ***
ACT GCA GCA TAA gctt
PstI——      Hind3—
```

FIG._6F.

ANTIFREEZE GENE Saf5, AS CLONED IN pUC119 (pLVC86)

```
                                           M   A   A   D
gaattcgagctcggt acc cgg gcc ATG GCT GCA GAC
EcoRI-       KpnI—        NcoI—
     SstI-       XmaI—              PstI—

T   A   S   D   A   A   A   A   A   A   L
ACT GCT AGC GAT GCC GCC GCG GCC GCT GCT TTG
    NheI—            SacII—
                         NotI—
              BglI—

T   A   A   N   A   A   A   A   A   A   L
ACA GCT GCT AAC GCC GCC GCG GCC GCT GCT TTG
 PvuII—              SacII—
                         NotI—
              BglI—

T   A   A   N   A   A   A   A   A   A   L
ACA GCT GCT AAC GCC GCC GCG GCC GCT GCT TTG
 PvuII—              SacII—
                         NotI—
              BglI—

T   A   A   N   A   A   A   A   A   A   L
ACA GCT GCT AAC GCC GCC GCG GCC GCT GCT TTG
 PvuII—              SacII—
                         NotI—
              BglI—

T   A   A   N   A   A   A   A   A   A   A
ACA GCT GCT AAC GCC GCC GCG GCA GCA GCA GCA
 PvuII—              SacII—
              BglI—

T   A   A  ***
ACT GCA GCA TAA gctt
 PstI—         Hind3—
```

FIG._6G.

ANTIFREEZE GENE Saf5, AS CLONED IN pRIT5 (pRLM105)

```
                          M   A   A   D
    gaattcc cgg gcc  ATG GCT GCA GAC
    EcoRI-           NcoI——
           XmaI——              PstI——

T   A   S   D   A   A   A   A   A   A   L
    ACT GCT AGC GAT GCC GCC GCG GCC GCT GCT TTG
        NheI——            SacII——
                              NotI——
                 BglI————————

T   A   A   N   A   A   A   A   A   A   L
    ACA GCT GCT AAC GCC GCC GCG GCC GCT GCT TTG
    PvuII——           SacII——
                          NotI——
             BglI————————

T   A   A   N   A   A   A   A   A   A   L
    ACA GCT GCT AAC GCC GCC GCG GCC GCT GCT TTG
    PvuII——           SacII——
                          NotI——
             BglI————————

T   A   A   N   A   A   A   A   A   A   L
    ACA GCT GCT AAC GCC GCC GCG GCC GCT GCT TTG
    PvuII——           SacII——
                          NotI——
             BglI————————

T   A   A   N   A   A   A   A   A   A   A
    ACA GCT GCT AAC GCC GCC GCG GCA GCA GCA GCA
    PvuII——           SacII——
             BglI————————

T   A   A  ***
    ACT GCA GCA TAA gctt
    PstI——       Hind3——
```

FIG._6H.

ANTIFREEZE GENE Saf6, AS CLONED IN pUCII9 (pGJ151)

```
                     P   G   T   M   D
GA ATT CGA GCT CGG TAC CCG GGT ACC ATG GAC
      SstI—      XmaI—      NcoI—
EcoRI—       KpnI—    KpnI—
 T   A   S   A   A   A   A   A   A   L
ACT GCT AGC GAT GCC GCC GCG GCC GCT GCT TTG
   NheI—              SacII—
                          NotI—
              BglI—

T   A   A   N   A   A   A   A   A   L
ACA GCT GCT AAC GCC GCC GCG GCC GCT GCT TTG
  PvuII—              SacII—
                          NotI—
              BglI—

T   A   A   N   A   A   A   A   A   A
ACA GCT GCT AAC GCC GCC GCG GCA GCA GCA GCA
  PvuII—              SacII—
              BglI—

T   A   A  ***
ACT GCA GCA TAA gctt
  PstI—      Hind3—
```

ANTIFREEZE GENE Saf6, AS CLONED IN pRIT5 (pLVC94)

```
                         M   D
         G AAT TCC CGG GCC ATG GAC
          EcoRI—         NcoI—
               XmaI—

T   A   S   D   A   A   A   A   A   A   L
ACT GCT AGC GAT GCC GCC GCG GCC GCT GCT TTG
   NheI—              SacII—
                          NotI—
              BglI—

T   A   A   N   A   A   A   A   A   L
ACA GCT GCT AAC GCC GCC GCG GCC GCT GCT TTG
  PvuII—              SacII—
                          NotI—
              BglI—

T   A   A   N   A   A   A   A   A   A
ACA GCT GCT AAC GCC GCC GCG GCA GCA GCA GCA
  PvuII—              SacII—
              BglI—

T   A   A  ***
ACT GCA GCA TAA gctt
  PstI—      Hind3—
```

FIG._6I.

ANTIFREEZE GENE Saf7, CLONED IN pUC119 (pGJ152)

```
                              P     G     T     M     D
     GA  ATT  CGA  GCT  CGG  TAC  CCG  GGT  ACC  ATG  GAC
              SstI——      XmaI——        NcoI——
     EcoRI——          KpnI——      KpnI——

T    A    S    D    A    A    A    A    A    A    L
     ACT  GCT  AGC  GAT  GCC  GCC  GCG  GCC  GCT  GCT  TTG
          NheI——                SacII——
                                    NotI——
                         BglI——————————

T    A    A    N    A    A    A    A    A    A    L
     ACA  GCT  GCT  AAC  GCC  GCC  GCG  GCC  GCT  GCT  TTG
     PvuII——                       SacII——
                                      NotI——
                         BglI——————————

T    A    A    N    A    A    A    A    A    A    L
     ACA  GCT  GCT  AAC  GCC  GCC  GCG  GCC  GCT  GCT  TTG
     PvuII——                       SacII——
                                      NotI——
                         BglI——————————

T    A    A    N    A    A    A    A    A    A    A
     ACA  GCT  GCT  AAC  GCC  GCC  GCG  GCA  GCA  GCA  GCA
     PvuII——                       SacII——
                         BglI——————————

T    A    A    ***
     ACT  GCA  GCA  TAA  gctt
     PstI——        Hind3——
```

FIG._6J.

ANTIFREEZE GENE Saf8, CLONED IN pUCII9 (pGMM3)

```
                                   P   G   T   M   D
     ga att cga gct cgg tac CCG GGT ACC ATG GAC
            SstI──        XmaI──      NcoI──
     EcoRI──     KpnI──       KpnI──

T   A   S   D   A   A   A   A   A   A   L
     ACT GCT AGC GAT GCC GCC GCG GCC GCT GCT TTG
         NheI──            SacII──
                             NotI──
                 BglI────────

T   A   A   N   A   A   A   A   A   A   L
     ACA GCT GCT AAC GCC GCC GCG GCC GCT GCT TTG
     PvuII──          SacII──
                             NotI──
                 BglI────────

T   A   A   N   A   A   A   A   A   A
     ACA GCT GCT AAC GCC GCC GCG GCA GCA GCA GCA
     PvuII──          SacII──
                 BglI────────

T   A   R   *
     ACT GCA CGT TAA caa catcc ggatcc aagctt
         HpaI──        FokI─ BamHI
                 MroI──            Hind3─
```

FIG.─6K.

ANTIFREEZE GENE Saf8, CLONED IN pUC119 (pGMM3)

```
                          P   G   T   M   D
ga att cga gct cgg vac  CCG GGT ACC ATG GAC
     SstI——           XmaI——      NcoI——
EcoRI——           KpnI——      KpnI——
```

```
 T   A   S   D   A   A   A   A   A   A   L
ACT GCT AGC GAT GCC GCC GCG GCC GCT GCT TTG
    NheI——              SacII——
                           NotI——
               BglI——
```

```
 T   A   A   N   A   A   A   A   A   A   L
ACA GCT GCT AAC GCC GCC GCG GCC GCT GCT TTG
PvuII——             SacII——
                       NotI——
           BglI——
```

```
 T   A   A   N   A   A   A   A   A   A
ACA GCT GCT AAC GCC GCC GCG GCA GCA GCA GCA
PvuII——             SacII——
           BglI——
```

```
 T   A   R   *
ACT GCA CGT TAA caa catcc ggatcc aagctt
       HpaI——      FokI—  BamHI
                MroI——        Hind3—
```

ANTIFREEZE GENE Saf8, AS CLONED IN pRIT5 (CONSTRUCT IS pLVC95)

```
                        M   D
G AAT TCC CGG GCC ATG GAC
 EcoRI——          NcoI——
      XmaI——
```

```
 T   A   S   D   A   A   A   A   A   A   L
ACT GCT AGC GAT GCC GCC GCG GCC GCT GCT TTG
    NheI——              SacII——
                           NotI——
               BglI——
```

```
 T   A   A   N   A   A   A   A   A   A   L
ACA GCT GCT AAC GCC GCC GCG GCC GCT GCT TTG
PvuII——             SacII——
                       NotI——
           BglI——
```

```
 T   A   A   N   A   A   A   A   A   A
ACA GCT GCT AAC GCC GCC GCG GCA GCA GCA GCA
PvuII——             SacII——
           BglI——
```

```
 T   A   R   *
ACT GCA CGT TAA caa catcc ggatcc aagctt
       HpaI——      FokI—  BamHI
                MroI——        Hind3—
```

FIG._6L.

ANTIFREEZE GENE Saf9, CLONED IN pUC119 (pGMM4)

```
                                    P   G   T   M   D
     ga att cga gct cgg tac CCG GGT ACC ATG GAC
            SstI——        XmaI——    NcoI——
     EcoRI——       KpnI——      KpnI——

T   A   S   D   A   A   A   A   A   A   L
     ACT GCT AGC GAT GCC GCC GCG GCC GCT GCT TTG
         NheI——          SacII——
                             NotI———
                   BgII————

T   A   A   N   A   A   A   A   A   A   L
     ACA GCT GCT AAC GCC GCC GCG GCC GCT GCT TTG
     PvuII——             SacII——
                             NotI———
                   BgII————

T   A   A   N   A   A   A   A   A   A   L
     ACA GCT GCT AAC GCC GCC GCG GCC GCT GCT TTG
     PvuII——             SacII——
                             NotI———
                   BgII————

T   A   A   N   A   A   A   A   A   A   A
     ACA GCT GCT AAC GCC GCC GCG GCA GCA GCA GCA
     PvuII——             SacII——
                   BgII————

T   A   R   *
     ACT GCA CGT TAA caa catcc ggatcc aagctt
         HpaI——        FokI- BamHI
                  MroI——        Hind3-
```

FIG.—6M.

ANTIFREEZE GENE Saf10, AS CLONED IN UC119 (CONSTRUCT IS GMM5)

```
                          P    G    T    M    D
    ga att cga gct cgg vac CCG  GGT  ACC  ATG  GAC
         SstI—        XmaI—         NcoI——
    EcoRI—       KpnI—      KpnI—

T    A    S    D    A    A    A    A    A    A    L
    ACT  GCT  AGC  GAT  GCC  GCC  GCG  GCC  GCT  GCT  TTG
         NheI—              SacII—
                            NotI——
                       BglI—

T    A    A    N    A    A    A    A    A    A    L
    ACA  GCT  GCT  AAC  GCC  GCC  GCG  GCC  GCT  AAA  CTG
         PvuII—             SacII—
                            NotI——
                       BglI—

T    A    D    N    A    A    A    A    A    A
    ACT  GCA  GAT  AAT  GCT  GCC  GCG  GCA  GCA  GCA  GCA
         PstI—              SacII—

T    A    R    *
    ACT  GCA  CGT  TAA  gaa catcc ggatcc aagctt
              HpaI—       FokI- BamHI
                          MroI—     Hind3-
```

ANTIFREEZE GENE Saf10, AS CLONED FROM GMM5 INTO pGMM8 (CONSTRUCT IS pGMM9)

```
                     G    N    S    M    D
                    GGG  AAT  TCC  ATG  GAC
                                   NcoI—
              EcoRI—

T    A    S    D    A    A    A    A    A    A    L
    ACT  GCT  AGC  GAT  GCC  GCC  GCG  GCC  GCT  GCT  TTG
         NheI—              SacII—
                            NotI——
                       BglI—

T    A    A    N    A    A    A    A    A    K    L
    ACA  GCT  GCT  AAC  GCC  GCC  GCG  GCC  GCT  AAA  CTG
         PvuII—             SacII—
                            NotI——
                       BglI—

T    A    D    N    A    A    A    A    A    A
    ACT  GCA  GAT  AAT  GCT  GCC  GCG  GCA  GCA  GCA  GCA
         PstI—              SacII—

T    A    R    *
    ACT  GCA  CGT  TAA  caa cat ccg gat cct gca gat atc gata
              HpaI—       FokI—        PstI—    ClaI—
                          MroI—                 EcoRV—
```

FIG._6N.

ANTIFREEZE GENE Saf10, AS CLONED WITH FACTOR X-a SITE IN pUC19
(CONSTRUCT IS pGMM7)

```
       N    S    R    V    D    I    E    G    R    D
    G AAT  TCC  CGG  GTC  GAC  ATT  GAA  GGT  CGC  GAC
    EcoRI─      SalI─                     NruI─
         XmaI─
                          FACTORXa───────

T    A    S    D    A    A    A    A    A    L
      ACT  GCT  AGC  GAT  GCC  GCC  GCG  GCC  GCT  GCT  TTG
         NheI─              SacII─
                              NotI─
                Bgl I─

T    A    A    N    A    A    A    A    A    K    L
      ACA  GCT  GCT  AAC  GCC  GCC  GCG  GCC  GCT  AAA  CTG
      PvuII─                Sac II─
                              NotI─
                BglI─

T    A    D    N    A    A    A    A    A    A
      ACT  GCA  GAT  AAT  GCT  GCC  GCG  GCA  GCA  GCA  GCA
      PstI─                   SacII─

T    A    R    +
      ACT  GCA  CGT  TAA  caa  catcc  ggatcc  aagctt
              HpaI─         FokI- BamHI
                               MroI─      Hind3-
```

FIG._60.

ANTIFREEZE GENE Saf10, AS CLONED WITH FACTOR X-a SITE FROM pGMM7
INTO pGMM8 (CONSTRUCT IS pGMM10)

```
       N    S    R    V    D    I    E    G    R    D
    3 AAT  TCC  CGG  GTC  GAC  ATT  GAA  GGT  CGC  GAC
    EcoRI—         Sal I—                   NruI—
           XmaI—
                                FACTORXa—

T    A    S    D    A    A    A    A    A    L
      ACT  GCT  AGC  GAT  GCC  GCC  GCG  GCC  GCT  GCT  TTG
           NheI—            Sac II—
                                  NotI—
              BglI—

T    A    A    N    A    A    A    A    A    K    L
      ACA  GCT  GCT  AAC  GCC  GCC  GCG  GCC  GCT  AAA  CTG
      PvuII—                   SacII—
                                  NotI—
              BglI—

T    A    D    N    A    A    A    A    A    A
      ACT  GCA  GAT  AAT  GCT  GCC  GCG  GCA  GCA  GCA  GCA
      PstI—                     SacII—

T    A    R    +
      ACT  GCA  CGT  TAA  caa  cat  ccg  gat  cct  gca  gat  atc  gata
                     HpaI—         FokI—         PstI—          ClaI—
                              MroI—                      EcoRV—
                                       BamHI—
```

FIG.—6P.

SET #1 SAF/H₂O
1-1
        −SAF              +SAF
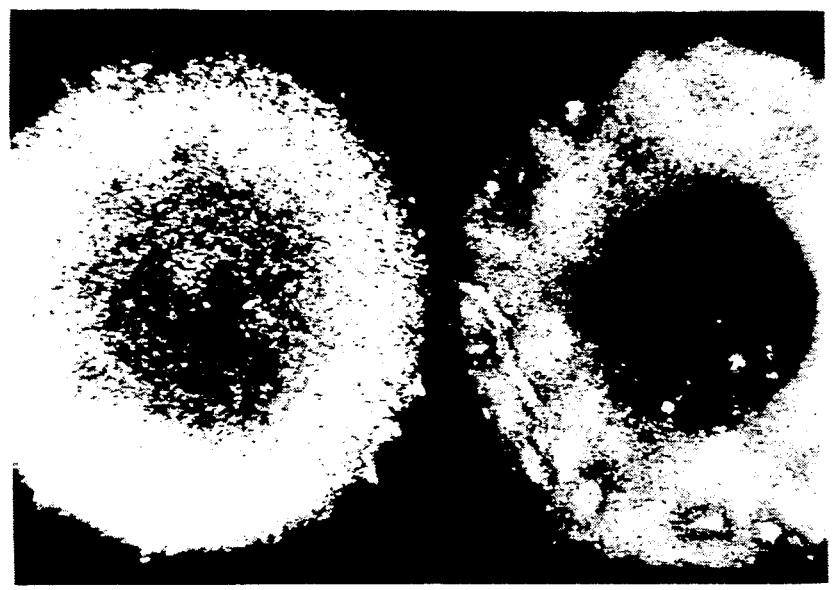
5 MIN
1-2   −SAF              +SAF
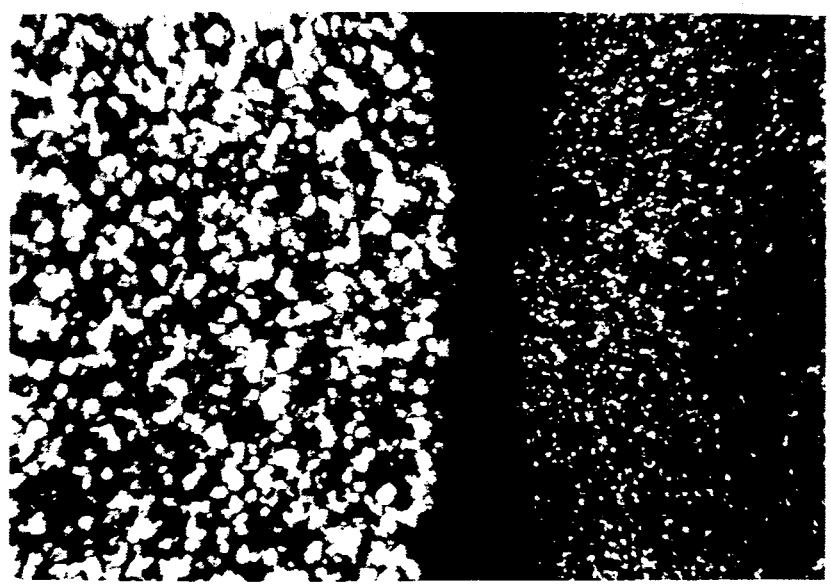
15 MIN
FIG._7A.

I-3  −SAF  +SAF
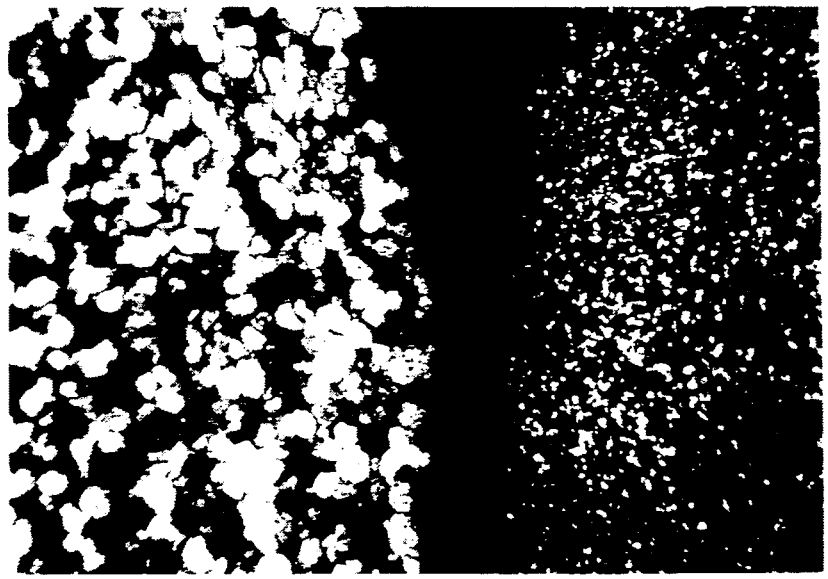
30 MIN
I-4  −SAF  +SAF
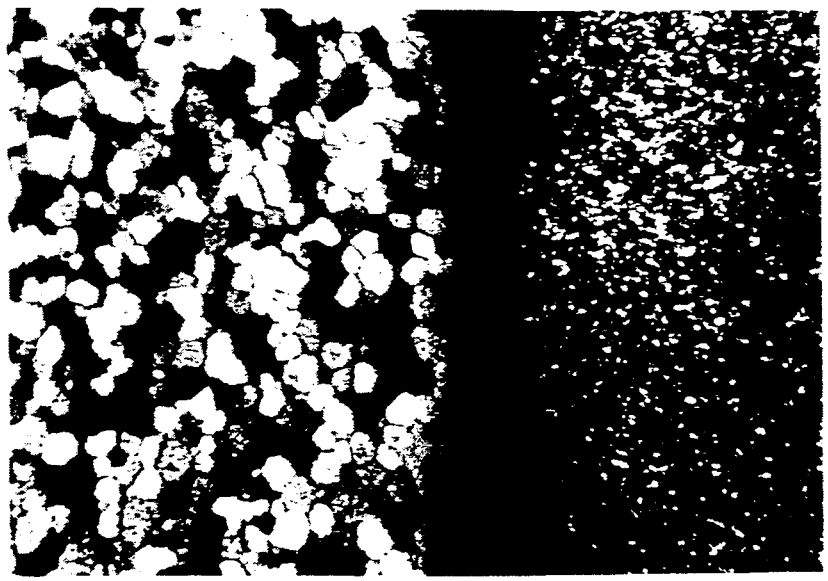
1 HR.
FIG._7A.

SET #2 SAF/POPSICLE
2-1 −SAF +SAF
5 MIN
2-2 −SAF +SAF
15 MIN
FIG._7B.

2-3   −SAF                +SAF
30 MIN
2-4   −SAF                +SAF
1 HR.
FIG._7B.

SET #3 SAF/A & W ROOT BEER FLOAT BAR
3-1    −SAF    +SAF
5 MIN.
3-2    −SAF    +SAF
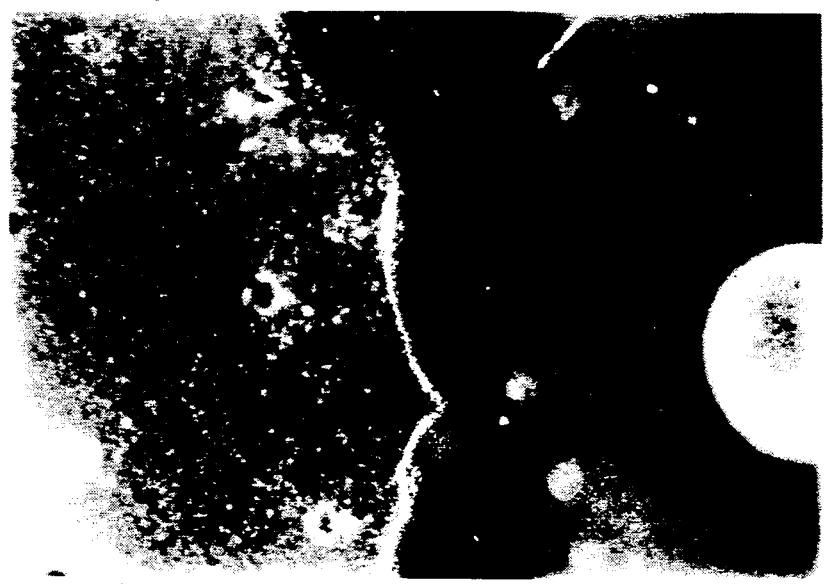
15 MIN.
FIG._7C.

3-3      −SAF                            +SAF
30 MIN
3-4      −SAF                            +SAF
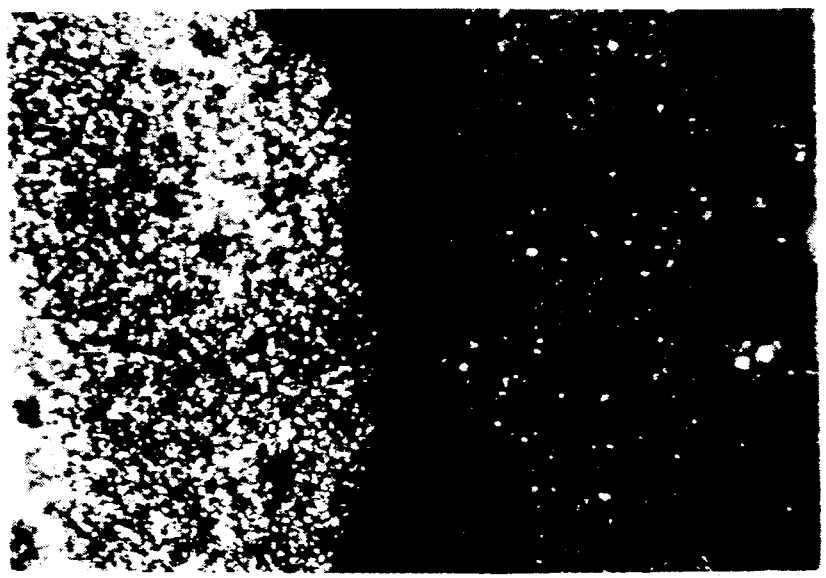
1 HR.
FIG._7C.

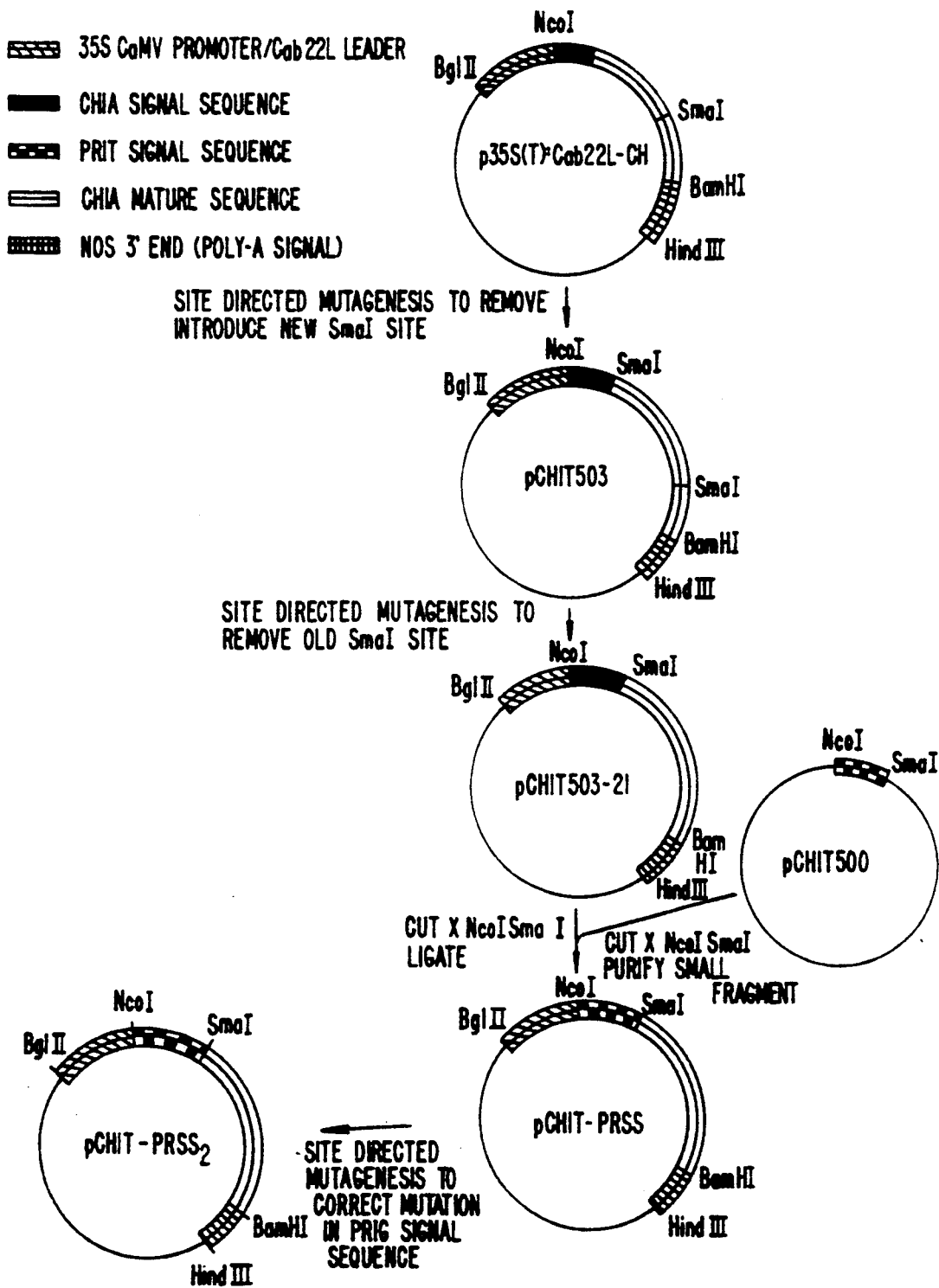
FIG._8A.

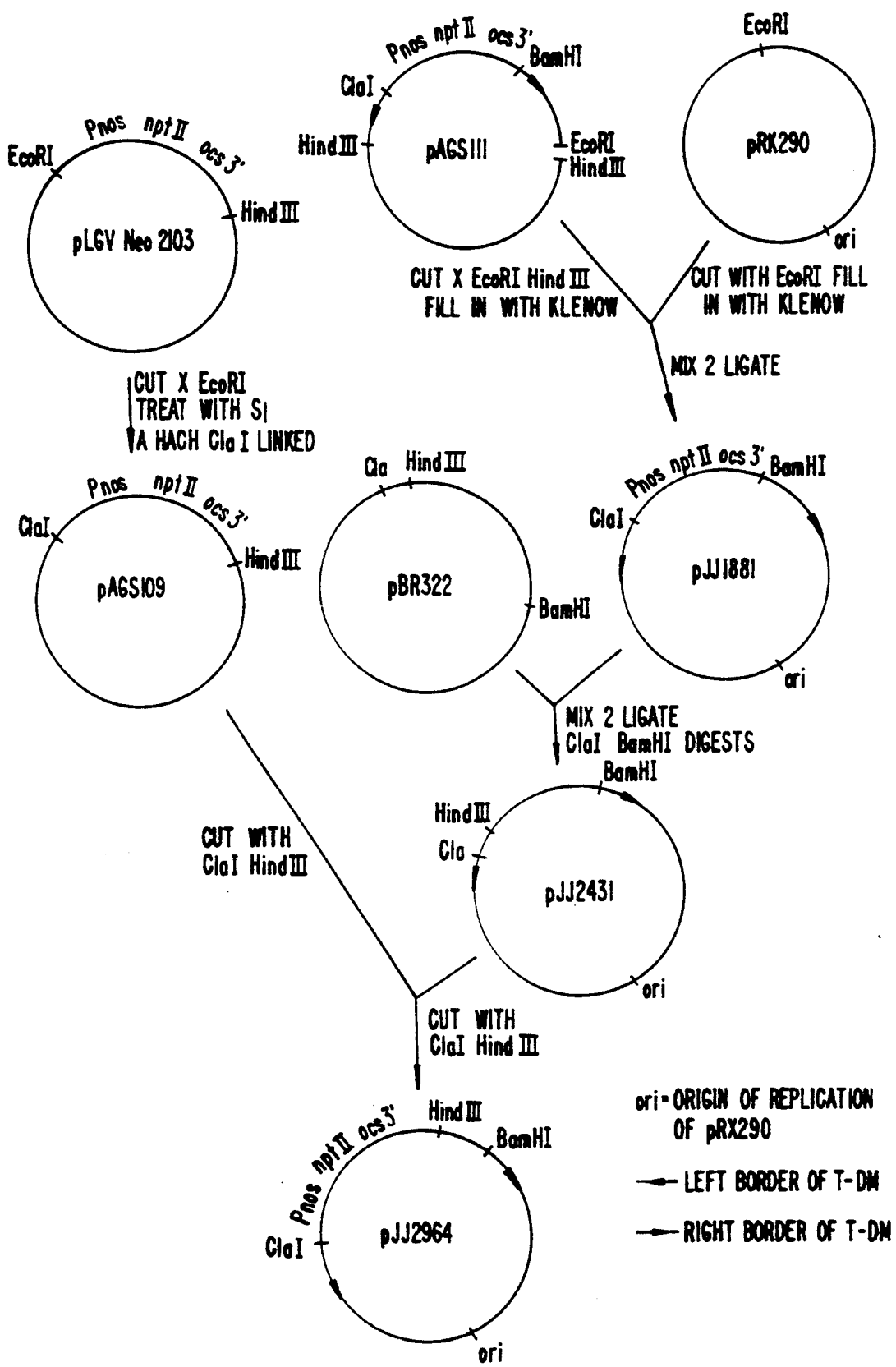
FIG._8B.

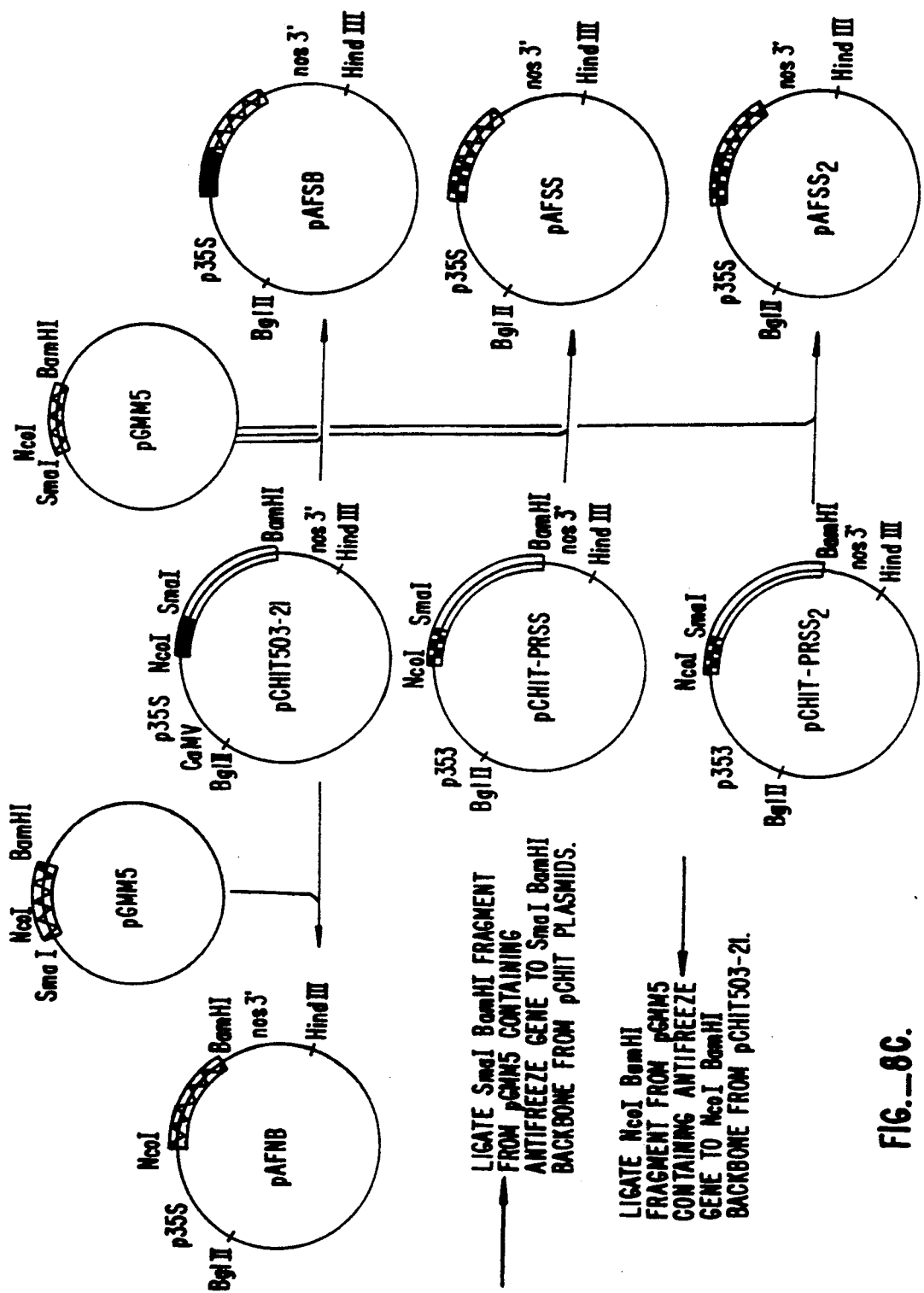
FIG._8C.

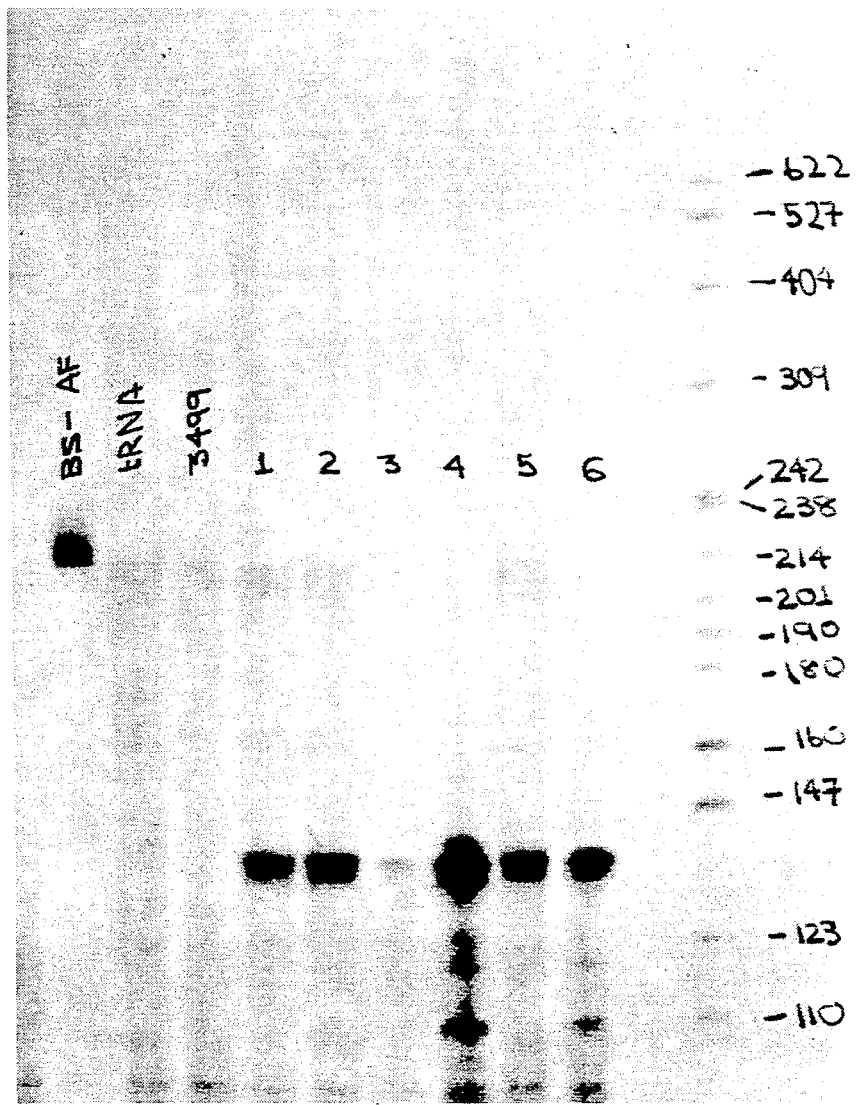
FIG._9.

ICE CRYSTAL GROWTH SUPPRESSION POLYPEPTIDES AND METHOD OF MAKING

FIELD OF THE INVENTION

This invention relates generally to reagents useful in improving the freezing tolerance of otherwise sensitive organic materials. These reagents increase the frozen storage life of, e.g., foodstuffs and other biological materials and maximize retention of various properties during storage or upon exposure to freezing.

BACKGROUND OF THE INVENTION

In modern times, refrigeration and, particularly, freezing have become common and preferred means for storage of biological materials. While refrigeration preserves some important properties of the samples, others continue to deteriorate at a slow but significant rate. Frozen storage may arrest most of this deterioration, but the combination of freezing and thawing introduces other changes which destroy other important properties.

In the modern world, frozen foods have become a mainstay of the human diet. To ensure a high quality product, sufficient for the demanding consumer's palate, frozen vegetables in particular, and frozen desserts, such as ice cream, have been the subject of extensive research by food processors. It is now known that recrystallization can have a substantial negative impact on the taste and texture of frozen foods. The advent of frost-free freezers has exacerbated this situation, which has been more traditionally associated with temperature fluctuations during transportation. After a relatively short period of time at other than sub-zero temperatures or even at sustained freezing temperatures, many frozen foods become less desirable, or worse, totally unsuitable, for human consumption.

While a variety of techniques have been implemented to mitigate the damages associated with recrystallization, and limited success has been attained, significant problems remain. Often, modifications to the processing of the frozen foods drastically affect their quality, color, flavor, and/or texture. Moreover, the additional processing can be very expensive and time consuming, rendering the techniques uneconomical. Similar difficulties have been associated with incorporating additives to the foodstuffs.

For biologics, such as therapeutic drugs, blood plasma, mammalian cells for use in tissue culture, and the like, freezing can cause extensive damage. For example, the freezing process itself kills most eukaryotic cells, and cells subjected to even one freezing and thawing cycle exhibit greatly reduced viability. Impaired function of living cells is also prevalent in tissue cryopreservation, with concomitant drawbacks for organ transplants. Similarly, frost or other freezing damage to plants presents a serious problem in agriculture. Finally, drugs can become ineffective, or even dangerous, if not maintained under required strict temperature conditions.

Thus, there exists a need for new techniques and compositions suitable for improving the preservation characteristics of organic materials at low temperatures, including storage of frozen foods and the viability of biologics. Ideally, these techniques and compositions will be inexpensive, yet completely safe and suitable for human consumption or in vivo therapeutic uses. The present invention fulfills these and other needs.

SUMMARY OF THE INVENTION

The present invention provides new and effective means to avoid many of the destructive effects of freezing and is widely applicable in its various embodiments to maximize retention of important properties of organic materials through the freezing and thawing processes. Its various embodiments address, inter alia, food storage, cryoprotection of medicinally used biologics and protection of agriculturally valuable plant products.

In one aspect, present invention provides novel methods and compositions for improving frozen storage life and other characteristics of organics and biological materials, such as frozen foods and biologics, through use of antifreeze polypeptides, preferably in substantially pure form. They further may be used in protecting agricultural products from damage from freezing climatic conditions. The preferred antifreeze polypeptides will typically comprise at least about 2 segments with sequences homologous to a consensus sequence, LTAAN AAAAAA, as well as additional amino acid segments or moieties, dependent upon desired additional characteristics. Among other uses, the antifreeze polypeptides assist in suppressing ice crystal growth in foodstuffs and biologics, without harming desirable aspects of the food or decreasing the viability of the biologic.

In another aspect, the invention relates to methods for producing novel compositions comprising the antifreeze polypeptides in combination with the organic materials. In other aspects, the invention relates to production of the antifreeze polypeptides, preferably by recombinant or chemically synthetic means. Specifically, cloning and expression of nucleic acid sequences encoding the polypeptides, their expression, purification and various methods of use are also provided.

BRIEF DESCRIPTION OF THE DRAWINGS

FIG. 1 shows the amino acid abbreviations.

FIG. 2 is a listing of the core repetitive sequences of the synthetic antifreeze polypeptides.

FIG. 3 is a listing of especially preferred antifreeze polypeptide sequences.

FIG. 4 is a listing of specific preferred antifreeze synthetic gene sequences and their corresponding amino acid sequences.

FIG. 5 is a list of fusion polypeptides and their uses.

FIGS. 6A-6P list the nucleotide sequences used to prepare the Saf and the saf genes.

FIGS. 7A-7C are the splat assay photographs for various uses of antifreeze polypeptides.

FIGS. 8A-8C describe the plasmid constructions for the plant transformations.

FIG. 9 is an autoradiograph of a gel showing expression in the plant transformation experiment. Results of the RNase protection experiment.

Lane 1: probe alone
Lane 2: Yeast tRNA
Lane 3: RNA from transformant not expressing antifreeze gene
Lane 4: RNA from 3499-APNB transformant #1
Lane 5: RNA from 2964-APNB transformant #2
Lane 6: RNA from 2964-APNB transformant #3
Lane 7: RNA from 2964-APNB transformant #4
Lane 8: RNA from 2964-APNB transformant #5

Lane 9: RNA from 2964-APNB transformant #6
Lane 10: pBR322 HpaII molecular weight markers

DETAILED DESCRIPTION OF THE PREFERRED EMBODIMENTS

In accordance with the present invention substantially pure polypeptides, typically free from, e.g., contaminating fish compounds, that exhibit ice crystal growth suppression activity are provided for use in improving or maintaining various characteristics of frozen or chilled foods and biologics. These antifreeze polypeptides can be of the formula $(NH_2)$ X1-X2- X3 (COOH), where X1 comprises a site specifically cleavable moiety, X2 is a polypeptide comprising at least two segments with a sequence homologous to a sequence LTAAN AAAAAA, and X3, if present, comprises a terminal amino acid sequence.

In one embodiment, X1 can consist essentially of:

a) a heterologous fusion partner polypeptide and, if present, a spacer segment;

b) a substantially stoichiometrically cleavable amino acid or polypeptide and, if present, one or more spacer segments;

c) a non-amino acid moiety; or d) oligopeptide segment other than an antifreeze segment typically between about 2 and 20 amino acids. Most preferably, X1 will comprise amino acid sequence which does not contain aspartate and X2 will comprise at least about 3 tandem segments, each of about 11 amino acids in length and comprising:

a) all alanines except between one and four substituted amino acids selected from the group of D, E, K, N, Q, R, S, T or L;

b) ten alanines, except having between one and four amino acid substitutes selected from the group of D, E, K, N, Q, R, S or T; or c) either seven alanines or six alanines with one leucine.

In one embodiment, antifreeze polypeptides will have an X1 region that is stoichiometrically cleavable by reagent, such as cyanogen bromide or an enzyme, preferably an enzyme that does not cleave the X2 region. Particularly preferred amino terminal segments comprise methionine, MAA, or IEGR. Typically, the X2 segments will be between about two and ten segments homologous to the consensus sequence and preferably three to five adjacent segments. A preferred amino acid segment within X2 will have the sequence DTASD AAAAA.

Similarly, X3, if present, may consist essentially of a fusion partner amino acid sequence with optional accompanying spacer segments or a terminal amino acid sequence. X3 will preferably comprise any of the following amino acid sequences: ATAA; ATAR; ATAK; ATAAAAR; or ATAAAAK.

The polypeptides are preferably produced by expressing recombinant nucleic acid sequences encoding the desired sequence. Typically, the antifreeze polypeptide will be less than about 7,000 daltons, but when fusion proteins are produced the molecular weight may exceed about 10,000 daltons, or more, depending upon the ultimate use. The recombinant nucleic acids typically comprise at least about 20 nucleotides which are homologous to nucleic acid sequences encoding an amino acid sequence of, e.g., FIG. 3, or which will hybridize under stringent conditions, of temperature or salt, to nucleic acid sequences encoding such amino acid sequences. Preferably, recombinant nucleic acid sequences will have synthetic segments having selected codon usage, comprising predetermined restriction or cleavage sites and further comprising sequences coding for newly introduced protease cleavage sites of the ultimate protein. The recombinant sequences preferably will be linked to a promoter sequence not normally associated with a naturally occurring polypeptide yet operable in a transformed host cell.

The polypeptides of the present invention are capable of minimizing potential freezing damage to a biologic or foodstuff compositions by adding a sufficient amount to suppress ice crystal growth. Various additives may also be incorporated in the compositions, particularly stabilizers for the added polypeptides.

The subject polypeptides may be added directly to the biologic or foodstuff in accordance with procedures well known to those skilled in the art. Alternatively, plants or cells may be transformed with recombinant nucleic acid sequences encoding the polypeptides, which will then be produced as desired, such as during the growth of a plant, particularly dicotyledonous.

Without intending to be bound by a particular mechanism, it is believed that the principle of ice crystal growth suppression is a non-colligative property of the antifreeze polypeptides involving interference with the addition of water to the ice lattice (adsorption inhibition) of an ice crystal. This mechanism is also seemingly different from the process which occurs upon initial nucleation or formation of the crystal. The rate of crystal growth determines the size of crystals while the nucleation rate determines the number of crystals.

In biological samples, much of the damage on freezing is due to the size or method of growth of the crystals. A larger number of very small crystals will normally be less damaging. The novel proteins of the present invention seemingly function to inhibit the addition of new water molecules to an ice crystal by binding to the growing crystal face and blocking sites for further crystal growth.

Thus, the subject polypeptide sequences are capable of suppressing growth and recrystallization of ice crystals in various organic materials. These antifreeze polypeptides have a number of distinctive properties and uses, as described more specifically below.

Antifreeze Polypeptides

The term "antifreeze polypeptide" refers to a polypeptide which exhibits the activity of inhibiting the growth of ice crystals. This activity is also referred to as ice crystal growth suppression. The growth-inhibited ice crystal will typically be at least about 10% to 20% smaller than non-inhibited ice crystals at a set point in time after onset of freezing, preferably at least about 50% smaller, and most preferably about 95 to 99% smaller. Though there are many ways to test for such an activity, the preferred method is to use a modified "splat assay" described below. Briefly, the assay consists of applying a solution of the protein to a cooled metal block and comparing the size of ice crystals formed after an appropriate time interval with a sample lacking the antifreeze polypeptide.

Preferably, the polypeptide sequences contain amino acid segments which exhibit strong homologies to particular consensus sequences. The single letter abbreviations are those commonly used by biochemists and listed in FIG. 1. See Stryer, *Biochemistry*, 3d Ed., W. H. Freeman & Company, New York (1988). Examples of these segments are listed in FIG. 2 and FIG. 3. The consensus sequence of one type is:

ITAan AaaAAa, where the capital letters are amino acids identically conserved in seven given segments and the lowercase letters are the most common amino acids in those positions. The blank is between the fifth and sixth amino acids merely for ease in counting how many amino acids are in the segment. Other useful segment sequences are given in FIG. 4. Homologous segments are those segments having sequences with greater than about 50% matching with the amino acids of the consensus sequence, typically greater than about 70%, and preferably greater than about 90%. All seven of the given segments in FIG. 2, type1 through type7, exhibit homology ranging from over 70% to total identity with the consensus sequence. Other segments which exhibit similar properties are listed in FIG. 4. Amino acid segments which exhibit homology to these segments of FIG. 2 or 4 are referred to as antifreeze segments These antifreeze segments may be modified but should, retain homology to the sequences in FIG. 2 or 4. They may be modified by substituting, preferably conservative amino acids, into various positions, preferably into the positions not identically conserved in the listed segments of FIG. 2. By conservative substitutions are meant substitutions within the groups as follows: gly, ala; val, ile, leu; asp, glu; asn, gln; ser, thr; lys, arg; and phe, tyr.

Thus, antifreeze polypeptides will typically contain two or more antifreeze segments, each preferably about eleven amino acids in length. In the absence of additional components, the antifreeze polypeptide component portion will vary from at least about 2,200 daltons to about 10,000 daltons, typically between about 3,000 and 7,000 daltons, and preferably about 3,500 to 6,000 daltons.

Multiple antifreeze segments are typically found in tandem, but may still retain activity with intervening amino acid segments between them. Although not intended as a limitation, there are indications that intervening segments most likely should preserve a conformational constraint within the antifreeze segments, and the likely limitations on intervening spacer segments require a multiple of about three and two thirds amino acid residues (meaning, e.g., three, four, seven, eight, eleven, fourteen, fifteen, etc...). The antifreeze polypeptide may retain its activity to suppress ice crystal growth even having an occasional insertion or deletion of an amino acid in a segment, though there may be limitations on the possible modifications consistent with retention of activity. At least two of these homologous antifreeze segments will usually be contained within the polypeptides of the present invention. One particular segment may be present in greater than one copy.

An antifreeze polypeptide may have as many as ten or more segments, but usually less than seven and in the preferred embodiment, three through five. The number of homologous segments may determine the effectiveness of a single molecule in suppressing crystal growth, or may determine the molar number of molecules necessary to have an effect.

The amino terminus of the polypeptide will typically comprise a site specifically cleavable moiety comprising one or more amino acids, preferably amino acid sequences selected from the group of:

a) M (methionine);
b) MAA;
c) a spacer segment containing the sequence IEGR;
d) amino acid sequences susceptible to site specific cleavage; and
e) an amino acid sequence which serves as a fusion peptide, thereby possibly conferring multifunctional character to the fusion polypeptide. These amino terminal sequences will typically confer resistance to proteolytic degradation of the antifreeze segments, but may also, or alternatively, confer a second biological or other activity. The moiety may also be a non-peptide extension such as a sugar, such as glucose, galactose and fucose, or be composed of a polymer of such sugars.

Methionine, by itself, is easily removable by treatment with cyanogen bromide, and thus falls into both categories (a) and (d). MAA, or methionine-alanine-alanine is a short, simple hydrophobic amino acid sequence. IEGR serves as a spacer and is the recognition and cleavage site for factor $X_a$ of the blood clotting cascade.

The moiety susceptible to site specific cleavage typically can be site specifically cut in a simple process, while not cleaving internally in the antifreeze segments so as to preserve the ice crystal growth suppression activity. Cleavage need not be stoichiometric, but will usually be nearly quantitative. While it need not be a single step reaction, preferably the process will not require a complex series of reagents. Simplicity can be conferred by a steady state type reaction system, or possibly by passing through a column wherein proteolytic enzymes will function on the sample as it passes through.

The means for site specific cleavage will generally include enzymatic cleavage. For polypeptides, this will typically be performed by site-specific proteases, which exhibit specificity in recognition and cutting of particular amino acid sequences. Exemplary proteases include trypsin, chymotrypsin, pepsin, papain, subtilisin, elastase or V8 protease. An alternative method is to treat with a chemical agent which causes breakage at a particular site. A classic example is the use of cyanogen bromide to cleave methionine, a reaction exhibiting high selectivity.

The carboxy-terminus of the antifreeze polypeptide will normally be:

i) ATAA;
ii) ATAR;
iii) ATAK;
iv) ATAAAAAR; or
v) ATAAAAAK.

Although these are the preferred terminal sequences, other sequences may be substituted. These are generally somewhat hydrophobic, but others may be utilized. The most common fusions will be segments which will confer onto the resultant protein particular advantageous properties, as indicated for resistance to destruction or degradation. See FIG. 5. Also envisioned in the invention are polypeptides having modifications to the polypeptide chain, including acetylations, methylations, derivatizations and glycosylations where the polypeptides have antifreeze properties. These modifications may be located either in the antifreeze segments or on other segments or both.

If desired, a heterologous fusion protein may comprise additional polypeptide or other segments attached to the amino- or carboxy-terminus (or both) of the antifreeze polypeptide. Surprisingly, the antifreeze activity of the antifreeze segments is retained, even when the segments are embedded in a fusion protein. The fusion protein of the present invention will normally comprise one or more domains from a heterologous protein, such as a protein which is normally targeted to a particular cellular compartment, into which the homologous antifreeze polypeptides or antifreeze segments are to be introduced. This site-specific targeting may provide improved production, such as through easier purification or secretion from a host (which, if desired, can involve cleavage of the targeting component as part of the secretion process). It may also be utilized to target these polypeptides to particular cell types. Targeting may be important for efficacy of the product. Another desirable property of the fusion partner polypeptide may be a particular affinity or reactivity. This affinity may provide improved detectability or production, such as through easier purification (e.g., by affinity chromatography) or measurement (e.g., by Western blots or enzyme assays).

In one embodiment of the invention, the fusion segment will confer onto the antifreeze segment the property of being directed or transported to a predetermined cellular compartment. Such segments are specifically intended to exclude homologous antifreeze protein signal sequences. Various examples include yeast alpha-factor which will be secreted, ribulose bisphosphate carboxylase which will be transported into the chloroplasts, phytohemagglutinin which is transported into vacuoles, cytochrome c which is transported into mitochondria, alpha-amylase which is secreted from monocotyledonous plants and pathogenesis-related protein PR1B which is secreted from dicotyledonous plants. In particular, there might be viral proteins which might be targeted to the nucleus and will confer greater resistance to significant freezing induced degradation of the nucleic acids or other components of the nucleus.

In another type of fusion protein, the antifreeze segments might be coupled to a targeting component which has selectivity for attachment or integration into particular cell types. The targeting of the antifreeze activity to specific cell types greatly increases the selectivity of protection. For example, after targeting, and upon freezing of a cell culture, those cells which have become cryoprotected might selectively survive the freezing process.

Other likely candidates for peptide fusions include, but are not limited to, Protein A, β-galactosidase, β-lactamase, chloramphenicol acetyltransferase, alcohol dehydrogenase, alpha amylase, luciferase, phytohemagglutinin, RuBPCase small subunit, phaseolin or yeast alpha mating factor. FIG. 5 provides a representative list, not comprehensive, of possible fusion proteins and their properties.

Nucleic Acids Coding For Antifreeze Polypeptides

A recombinant nucleic acid sequence results from the joining of two segments of nucleic acid which would not otherwise be joined in nature. Typically, the separate nucleic acid segments originate from different species, but may come from two different individuals, or even different cells of the same individual. The term "recombinant nucleic acid sequence" also includes a chemically synthesized nucleic acid segment having a selected sequence joined to another segment from any other source.

Typically, the synthetic segment is used instead of a natural source, because a particular nucleic acid sequence is desired which may be different from known natural sequences. Often a synthetic sequence is used to change a codon or to change codon usage, or to introduce or remove restriction enzyme recognition sites. Particular codon selection may be different for the purpose of higher translation efficiency in the target expression system making use of the differential codon usage of a given host, to avoid particular codons or to change the amino acid sequence of a resulting polypeptide. Introduction or removal of particular restriction enzyme recognition or cutting sites may be important to assist in the process of generating a particular sequence having desirable characteristics, including the introduction or removal of new or different sequence segments. It may also be utilized to introduce a new sequence, for example, new protease cleavage sites.

Synthetic segments are particularly useful in view of the general repetitive nature of the antifreeze segments. By appropriate design of the nucleic acid segments making up the repeats, it is possible to generate various nucleic acid segments encoding individual segments but with specific restriction enzyme cut sites. By selection of the appropriate enzymes, it is possible to simply introduce particular coding sequences into previously made antifreeze polypeptides. Thus, the possibility of mixing and matching combinations of the segments may be readily achieved, making the testing of the various combinations much easier and faster.

Although the preferred embodiment of the nucleic acid encodes a single antifreeze segment with the restriction sites located at the ends, it is possible to have the restriction enzyme cut sites internal to the repeat segment with the introduced segment spanning the boundary of a particular repeat segment. Those skilled in the art will readily devise various modifications in this regard to the preferred sequences disclosed herein.

Thus, an alternative embodiment of the present invention includes recombinant nucleic acid sequences coding for engineered polypeptides containing the antifreeze segments as defined above. These recombinant nucleic acid sequences include segments which encode antifreeze polypeptides, e.g., of FIG. 2, 3 or 4, and homologous sequences. Homologous sequences will typically be at least about 70% homologous, preferably 80–90% or more.

The sequences also include nucleic acids encoding antifreeze polypeptides containing either fusion protein segments or segments which are engineered with additional desired sequences. This will include synthetic nucleic acid sequences which have incorporated unnatural sequences, typically for the purposes of substituting different codons, (particularly to match codon usage to the preferred codon usage of the expressing host cell) modifying the amino acid sequence of the resultant polypeptide, removing or adding restriction enzyme recognition or cutting sites or modifying upstream or downstream sequences in regulation of the expression of the polypeptide.

In particular, the preferred embodiments of the antifreeze segments contain, and are flanked by, recognition sites for restriction enzymes with hexa- and octa-nucleotide specificity. In particular, they are flanked by the following sites: EcoRI, SstI, SmaI, KpnI, MroI, BamHI, SphI, HindIII (not all sites flank any one gene). Also in particular, they contain the following sites: NcoI, NheI, BglI, SacII, NotI, PvuII, and HpaI. These sites are useful in the construction and manipulation of the antifreeze-coding sequences.

Furthermore, the codon usage of the preferred embodiments differ from that of the currently-known antifreeze genes from fish. Optimal codon usage will facilitate translation in each species targeted for expression of antifreeze genes. In particular, preferred codon usages in prokaryotes, in yeast, and in higher plants differ from the codon usage found in winter flounder antifreeze genes (Maruyama et al., Nucleic Acids Research, 14 Suppl. 151-189). More particularly, the codons GCA, GCG, and GCT together account for more than 65% of the alanine codons in known genes of *E. coli, S. cerevisiae*, and *Z. mays* whereas they account for less than 35% of the alanine codons in known antifreeze genes of winter flounder (*P. americanus*). Similarly, the codons ACA, ACG, and ACT together account for most of the threonine codons in known genes of *E. coli* (51%), *S. cerevisiae* (70%) and *Z. mays* (66%), whereas they account for less than 25% of the threonine codons in known antifreeze genes of *P. americanus*.

Placing a nucleic acid segment encoding the antifreeze polypeptide (e.g., between about 65 and 350 nucleotides) into a different surrounding sequence environment is contemplated, for example, to place the nucleic acid segment under the operational control of an upstream promoter or enhancer element. When a sequence is under operational control of the promoter, it is operably linked to the promoter. Operational linkage between the promoter and a coding sequence will normally exist when located within about a thousand nucleotides upstream of the ribosome binding site (if present), preferably within about five hundred nucleotides and most preferably within about three hundred nucleotides and at the distance wherein the promoter will have its most desirable effect.

The promoter will typically be chosen to be one which will result in strong transcription of the segment, oftentimes constitutively. A typical constitutive strong promoter is the 35S promoter of cauliflower mosaic virus. Other times, an inducible promoter will be desired. A typical inducible promoter is the lac promoter. In still other circumstances, a developmentally regulated promoter will be preferred, such as the RUBPCase small subunit promoter of plants. A promoter which is functional in the ultimate target host will be desired, but occasionally a different promoter might be selected.

A large assortment of vectors are available and may be appropriate depending upon the use intended. In the early research phase, some vectors, such as the pUC vectors or phage vectors, might be most appropriate due to their simplicity and efficiency in amplification of copies of the vector. In other stages, expression vectors (typically between about 1,000 and 5,000 nucleotides or more) may be preferred, which may be operably linked to strong promoters ensuring that the nucleic acid sequence will be expressed producing large quantities of polypeptide.

For expression in *E. coli*, a vector containing the tryptophan promoter may be a preferred vector having a high expression level. Other similar promoters will be the β-galactosidase promoter or the promoter in phage λ. Properties useful or important in selection of the promoter or the vector are addressed in Maniatis et al. *Molecular Cloning, A Laboratory Manual*, Cold Spring Harbor Laboratoy (1982), hereafter referred to as Maniatis. Plasmids or phage will typically be the preferred vectors for bacteria.

One particular system which will allow high message level expression with particularly low levels of contaminating message is the T7 polymerase system. *E. coli* is co-transformed with a coding segment operably linked to a T7 promoter and with an inducible and rifampicin insensitive T7 polymerase. Upon induction of the polymerase in the presence of rifampicin, highly specific transcription of the intended sequence will result.

For expression in eukaryotic cells, especially mammalian tissue culture cells, promoters such as the SV40 T antigen, thymidine kinase or β-globin might be preferred. Particular yeast promoters, which might be selected include the GAL1,10 (*Mol. & Cell Biol.* (1984) 4:1440-1448), ADH 2 (*J. Biol. Chem.*, (1983) 258:2674-2682) and PH05 (*EMBO J.*, (1982) 6:675-680) promoters. In plant cells, preferred promoters include the 35S promoter from cauliflower mosaic virus, the promoter for the small subunit of ribulose bisphosphate carboxylase (RuBPCase) and the nopaline synthase promoter from *Agrobacterium tumefaciens*.

For high level expression, the insect baculovirus system can be very efficient. See Luckow & Summers (1988) *Bio/Technology*, 6:47-55. These vector systems typically allow for simple and efficient protein purification.

Production of Antifreeze Polypeptides

The primary ultimate use of this invention is the use of the antifreeze polypeptides to bind to ice crystal faces blocking the growth of the crystal. The inhibition of ice crystal growth requires the presence of the polypeptide, so production of the polypeptide is very important. Synthesis may be pursued in two forms, either biological or synthetic. The biological method is by expression of polypeptide coding sequence or gene; the synthetic method is by chemical synthesis of a polypeptide.

A preferred synthetic method utilizes solid phase peptide synthesis, such as that developed by Merrifield (*J. Am. Chem. Soc.*, (1963) 85:2149-2156). This method will be particularly useful in testing particular compositions or formulations for antifreeze activity.

For large scale production, the biological expression would typically be preferred. The encoding nucleic acid or gene can be a natural gene with recombinant modifications or a totally synthetic sequence that will be expressed in an appropriate expression system. The methods utilized for insertion of a natural sequence segment into an appropriate vector are well known to persons of ordinary skill in the art, see Maniatis or Wu, et al. (1987) *Methods in Enzymology*, Vol. 153, Academic Press, New York, N.Y.

Synthetic sequences can be synthesized by the phosphoramidite chemistry to make particular sections of the sequence (Beaucage and Carruthers, (1981) *Tet. Letters*, 22:1859-1862). Overlapping segments can be synthesized and then ligated together to produce a larger gene.

Finally, by selecting particular sequences for the antifreeze segments, restriction enzyme cutting sites may be introduced which will provide convenient segments which may be easily linked together or inserted to generate tandem repeats, as will be obvious to one of ordinary skill in the art.

Purification of the antifreeze polypeptides will be by methods known to a person of ordinary skill in the art of protein purification. Standard purification techniques may be from either cell lysates or culture medium if the proteins are secreted. Typical methods are column chromatography, ammonium sulfate salt precipitations, antibody affinity column chromatography and others. With naturally occurring polypeptides (e.g., produced in fish), a preferred method of purification is as described by DeVries et al. (1977) *Biochem Biophys. Acta* 495:388-392.

Preferably, the antifreeze polypeptides will be purified to substantial homogeneity, usually at least about 70% to 80% pure, preferably about 90-95% pure, most preferably 99% or more pure. Typically, the polypeptides will be substantially free of contaminating, naturally associated fish compounds.

Use of Antifreeze Polypeptides and Related Genes

The polypeptides or genes encoding the polypeptides may be used in ways to suppress ice crystal growth. The polypeptide may be introduced in the protein form, or it may be introduced as a gene which is expressed endogenously at a level which should be attainable by expressing an antifreeze protein in the plant cell under the control of a suitable strong promoter to produce the polypeptide(s). Suitable concentrations of antifreeze polypeptides will vary depending on the use, but will typically be in the range of from about one part per billion to about one part per thousand (i.e., 1 $\mu$g/l to 1 gm/l).

In one embodiment of the invention, the polypeptides will be introduced to foodstuffs. This has a number of different aspects. One is the introduction into plant foodstuffs, either into the entire plant and thus conferring some degree of general resistance to damage from subfreezing climatic conditions, or into a plant part such as the fruit or vegetable portion to minimize damage specifically to those particular plant organs upon freezing. Exemplary plant parts are stems, roots, leaves, flowers, petioles, pericarp, seeds, vegetative tissue, tubers and so forth.

The texture, taste, and useful storage life of frozen vegetables will be improved, for example, celery, potatoes, asparagus, peas, carrots, beans, broccoli, sweet corn and spinach. Similarly, the texture, taste and useful storage life of fruits will be enhanced, including strawberries, blueberries, raspberries, citrus fruits, bananas, grapes, kiwis, peaches, pineapples, plums, cherries, tomatoes and mangoes.

This introduction into plant and other products may be most easily accomplished by genetic introduction of appropriate nucleic acids into the target organism. Expression of the nucleic acid, either constitutively or inducibly, before food processing has begun, or after harvesting and processing has begun, may lead to sufficiently high levels of the polypeptide to effectively protect the foodstuff, such as up to about 0.1% of total plant protein by mass. Expression can also be on a tissue specific basis. For example, linkage to ripening genes in fruits may result in expression even after harvesting from the producing plant.

The polypeptides may also be added into foods which are expected to be frozen. Many frozen foods are intended to be consumed in the cold state, for example, ice cream, frozen yogurt, ice milk, sherbet, popsicles, frozen whipped cream, frozen cream pies, frozen puddings and the like. In particular, texture and flavor are adversely affected by the formation of large ice crystals throughout a freeze-thaw cycle that occurs in most home frost-free freezers or upon sustained storage in the frozen state. This ice crystal growth process may be prevented entirely, or at least minimized by the addition of antifreeze polypeptides. The antifreeze agent may be either incorporated throughout the foodstuff, or may, alternatively, be applied to the surface where condensation and crystal formation is expected to occur most readily.

Another important use is to transform dough yeast with nucleic acids encoding these proteins. Upon incorporation and expression of this gene into the yeast, and use of these yeast in frozen dough, the dough will naturally leaven upon thawing because the yeast viability will remain high upon thawing. Because less damage accumulates from storage in the presence of these antifreeze polypeptides and thawed samples preserve high viability, either longer storage times will be possible, or perhaps much smaller aliquots will need to be stored.

There are various embodiments not specific to the food area. One is the use of antifreeze proteins to protect plants from climatic freezing conditions. The antifreeze protein or polypeptide may be either internally incorporated into the cytoplasm by expression of an introduced gene, or the polypeptides may be externally applied to the plants. External application may be achieved either by direct application of the polypeptides to the plant, or by the external deposit onto the plant of an organism which secretes the polypeptide. These same alternatives for introduction apply to other uses as well.

Another embodiment is the introduction of an antifreeze polypeptide into liquid surrounding an organ, tissue or other biological sample. One particular use would be during transportation to a hospital for a transplantation operation or for storage purposes. The antifreeze polypeptide should allow short- or long-term storage at a subfreezing temperature, thereby minimizing inherent metabolism or degradation, but with substantially diminished cellular damage from ice crystal growth. Other medically important temperature sensitive biological samples are blood and blood products, therapeutic agents, protein drugs, bioassay reagents and vaccines.

Yet another embodiment is the introduction of an antifreeze polypeptide into cells or their extracts destined for frozen storage. For example, bacterial cells, yeast cells, plant cells and, most particularly, animal cells containing the antifreeze proteins have increased cell or tissue viability with minimal or no loss of inherent characteristics due to the freeze-thaw process. Subcellular samples or cellular extracts may have similar sensitivities to freezing, especially on prolonged storage. Typical examples will be in vitro protein translation systems, enzyme preparations, and particularly samples which contain sensitive membrane components, such as chloroplast or mitochondrial membrane preparations. In particular, samples containing organelles may display increased resistance to freezing damage upon addition of these antifreeze polypeptides. Soft animal tissues will exhibit less damage upon freezing in the presence of the subject polypeptides, and addition of the polypeptides will be useful in situations when cellular integrity upon freezing and subsequent thawing is important or desired, such as for tissue culture deposits. Thus, samples destined for frozen storage, such as for cell or tissue depositories, might routinely have the polypeptides added to them. Among the cell types often stored are genetic variants of bacteria, fungi (including yeast), and, particularly, higher eucaryote cells (such as hybridoma strains and tissue culture cell lines).

Antifreeze fusion polypeptides of the present invention may be targeted to a particular cellular compartment or to extracellular space, to a particular cell or to particular cell types. By attachment of polypeptide segments which specify or determine targeting to cellular compartments, the antifreeze segments may be targeted to a particular cellular organelle. Not only will the peptide be directed to the organelle, but the antifreeze function may remain functional even when surrounded by other polypeptide segments. By fusion to antibodies or other molecules having cell specificity in binding, the resistance to cellular damage upon freezing can be conferred to those cell types. This technique will also find use in organs.

Also included in the invention are compositions and uses based on the mixture of antifreeze polypeptides with stabilizers well known to those skilled in the art and other additives. These compounds may be present to inhibit decay, inhibit oxidation, prevent discoloration, inhibit microbial growth, stabilize emulsions and so forth.

Transformants Containing Antifreeze Polypeptide Genes

The natural or synthetic nucleic fragments coding for the antifreeze polypeptide will be incorporated in nucleic acid constructs capable of introduction to and/or expression in the ultimate target expressing cell. Usually, the nucleic acid constructs will be suitable for replication in a unicellular or multicellular host, such as yeast or bacteria, but may also be intended for introduction and integration within the genome of cultured mammalian or other eukaryotic cell lines, in particular, plants. Nucleic acid constructs prepared for introduction into bacteria or yeast will include a replication system recognized by the host, the nucleic acid fragment encoding the desired antifreeze polypeptide product, transcriptional and translational initiation regulatory sequences joined to the 5'-end of the antifreeze polypeptide encoding nucleic acid sequence, and transcriptional and translational termination regulatory sequences joined to the 3'-end of the sequence. The transcriptional regulatory sequences will include a heterologous promoter which is recognized by the host. Conveniently, available expression vectors which include the replication system and transcriptional and translational regulatory sequences together with an insertion site for the antifreeze polypeptide encoding sequence may be employed.

The gene will include any nucleic acid segment which contains a coding sequence for antifreeze polypeptide. Normally, the gene will include the coding sequence plus the upstream and downstream associated sequences, particularly any enhancer, promoter, ribosome binding site or transcription initiation markers. Downstream segments may also be important for message polyadenylation and processing, and thus are also contemplated in the usual instance.

The introduction of genes into cells or groups of cells for expression is another method for generally introducing the polypeptides into the sample of interest. The end product of the transformation is also included as the product of this invention, and the term "transformed cell" will include the actual cell transformed, and all progeny of that cell. In the typical case, the final organism will contain cells, each of which will contain the gene. Standard transformation procedures exist for bacteria (Maniatis), fungi (Sherman et al. (1986) in *Laboratory Course Manual for Methods in Yeast Genetics* CSH), plants (van den Elzen et al. (1985) *Plant Mol. Biol.*, 5:149-154) and animals (Hanahan, (1988) *Ann. Rev. Genetics*, 22:479-519).

New Antifreeze Genes or Polypeptides

The present invention also provides means for generating or isolating new polypeptides which will exhibit the ice crystal growth suppression activity. Discovering such polypeptides typically requires an accurate and, preferably, quick means for assaying the activity.

The method of choice is a "splat assay" modified from Knight et al. (1988) *Cryobiology*, 25:55-60. Recrystallization involves the growth of some crystals at the expense of others. Typically, growth is in the form of long thin spicules, (see DeVries (1983) "Antifreeze peptides and Glycopeptides in Cold-Water Fish" in *Ann. Rev. Physiol.*, 45:245-260, FIG. 1) which can pierce and destroy sensitive lipid membranes. The splat assay is comprised of dropping a small droplet of a solution of the polypeptide in an appropriate buffer onto a cooled plate. The droplet "splats" onto the plate surface, freezes rapidly forming many small crystals and the recrystallization process is monitored visually after an appropriate time interval. Samples containing the antifreeze polypeptide exhibit a much decreased crystal size.

Synthetic homologous polypeptides may be assayed to determine what particular characteristics or sequences will be most effective. Alternatively, since the segments themselves are encoded in easily manipulated synthetic nucleic acid segments, insertions, deletions or substitutions into existing sequences are readily prepared, expressed and assayed.

In another embodiment of the present invention, antibodies against epitopes contained in the antifreeze segments may be raised to search for similar polypeptide sequences in other naturally occurring proteins. Besides arctic or cold water fishes, insects or other organisms which are naturally exposed to subfreezing temperatures may be scrutinized for content of proteins possessing antifreeze properties. Alternatively, the genes or nucleic acids encoding known segments can be used to select homologous nucleic acid segments, a somewhat preferred method because expression is unnecessary. An antibody screen will be dependent on polypeptide expression, which may be developmentally or conditionally dependent.

Another method for selecting new polypeptides is to mutagenize known segments and assay the resultant product. While the splat assay is also useful here, a simpler freeze-thaw cycle of expressing cells may select for those cells least sensitive to the freezing process; generally due to the expression of an effective antifreeze polypeptide.

EXPERIMENTAL

The following experimental section is offered by way of example and not by limitation.

In general, preparation of plasmid DNA, restriction enzyme digestion, agarose and polyacrylamide gel electrophoresis of DNA, DNA recovery from the gels, Southern blots, Northern blots after separation of the RNA on a formaldehyde-agarose gel, DNA ligation and bacterial transformation were carried out using standard methods. Maniatis et al. (ed.), *Molecular Cloning, A Laboratory Manual*, Cold Spring Harbor Laboratory (1982), hereafter referred to as Maniatis and herein incorporated by reference. Similar procedures are described in Wu et al. (ed). *Recombinant DNA Methodology*, Academic Press (1989). The following abbreviations are used: synthetic antifreeze polypeptide encoding DNA, saf; synthetic antifreeze polypeptide, Saf; betalactamase encoding DNA, bla; Staphylococcal Protein A encoding DNA, Spa. Note that the composition of Saf3 through Saf10 are contained in FIG. 3. Sizes of nucleic acids are given in kbp, which refer to kilobase pairs where double stranded.

EXAMPLE 1: Inhibition of recrystallization by a Betalactamase-Saf3-Betalactamase fusion protein A. Construction of the synthetic antifreeze gene saf3

Two DNA sequences of 71 and 63 bases respectively were synthesized chemically and annealed together to produce the double-stranded oligonucleotide with staggered ends shown as DS oligo 1 (see FIG. 6). DS oligo 1 was cloned between the XmaI and PstI sites of vector pUC118 to yield plasmid pLVC74.

Two DNA sequences each of 49 bases were synthesized chemically and annealed together to produce the double-stranded oligonucleotide with staggered ends shown as DS oligo 2 (see FIG. 6). DS oligo 2 was cloned between the KpnI and PstI sites of vector pUC118 to yield plasmid pLVC73.

Plasmid pLVC73 was treated with restriction enzyme SacII to release the double-stranded oligonucleotide with staggered ends shown as DS oligo 3 (see FIG. 6). DS oligo 3 was cloned into the SacII site of plasmid pLVC74 and the progeny were screened by sequencing to yield plasmid pLVC82, in which DS oligo 3 was shown to be inserted in the sense direction.

The SacII fragment in pLVC82 was reduplicated in direct orientation as described in this paragraph. The principle of reduplicating restriction fragments is described in Green et al. (1988) *Mol. Gen. Genet.*, 215:165-172. The DNA of plasmid pLVC82 was extracted from the Rec+ *E. coli* K22 strain SK1592 (Warren & Green, (1985) *J. Bacteriol.*, 161:1103-1111), subjected to agarose gel electrophoresis, and the band corresponding to plasmid dimers was excised and its DNA recovered; this dimeric pLVC82 was amplified by transformation into the recA- E. coli K12 strain JC10291 (Willis et al. (1981) *Mol. Gen. Genet.*, 183:497-504). Dimeric pLVC82 was digested partially by SacII and subjected to agarose gel electrophoresis; bands corresponding to approximately half the plasmid dimer were excised and their DNA recovered; the fragments of recovered DNA were recircularized by ligase treatment and transformed into strain JC10291.

The progeny of the SacII fragment-reduplication were screened by restriction analysis to find plasmid pLVC83, in which two copies of DS oligo 3 are present in tandem. The antifreeze-encoding sequences in pLVC83 are known as gene saf3.

B. Construction of the bla-saf3-bla gene fusion

Plasmid pLVC83 was treated with restriction enzyme PstI to release an approx. 0.1 kbp DNA fragment containing saf3 sequences. This short fragment was cloned into the PstI site of plasmid pBR322 (Balbas et al. (1986) *Gene*, 50:3-40) and the progeny were screened by restriction analysis to find plasmid pLVC84, in which the 0.1 kbp fragment was shown to be inserted into pBR322 in the indicated direction. This inserts saf3 into an internal position in the bla (Betalactamase-encoding) gene of pBR322 and maintains the reading frame from the upstream portion of bla through saf3 and into the downstream portion of bla.

C. The effect of the Betalactamase-Saf3-Betalactamase fusion protein on the recrystallization of ice Plasmids pLVC84 (carrying the gene fusion) and pBR322 (to provide nonfused Betalactamase for a negative control) were transformed into *E. coli* K12 strain JC10291. The resultant bacterial strains were grown at 37° C. in Luria broth (LB) to an optical density at 600 nm (O.D.$_{600}$) of approx. 1.0, harvested by centrifugation for 15 min. at 7000 rpm in an SS34 Sorvall rotor, and lysed by sonication in 10 mM EDTA/30 mM Tris-HCl pH 8.0. The resulting crude cell extracts were tested in parallel using the splat-cooling assay for recrystallization as described in detail under example 3 (Knight et al. (1988) *Cryobiology*, 25:55-60). Ice crystals grew to an average diameter more than five-fold greater in the negative controls compared to the samples containing the fusion protein. Thus it was shown that the extract containing the Betalactamase-Saf3-Betalactamase fusion protein inhibited recrystallization, whereas the negative control did not.

This demonstrated that a peptide antifreeze attached to foreign polypeptides at both its amino- and carboxy-termini can function to inhibit recrystallization.

EXAMPLE 2: Inhibition of recrystallization by a Protein A-Saf5 fusion protein and purification of said fusion protein A. Construction of the synthetic antifreeze gene saf5

Plasmid pLVC83 was treated with restriction enzymes EcoRI and HindIII to release an approximately 0.1 kbp DNA fragment containing saf3. This fragment was cloned between the EcoRI and HindIII sites of pUC119 to yield plasmid pGMM1. An internal SacII fragment of pGMM1 was reduplicated as described in example 1. The products of this manipulation were screened by restriction analysis to find plasmid pLVC85, in which three copies of DS oligo 3 are present in tandem. The synthetic sequences in pLVC85 are known as gene saf4. An internal SacII fragment of pLVC85 was reduplicated as described in example 1. The products of this manipulation were screened by restriction analysis to find plasmid pLVC86, in which four copies of DS oligo 3 are present in tandem. The antifreeze-encoding sequences in pLVC86 are known as gene saf5.

B. Construction of the spa-saf5 gene fusion

Plasmids pLVC86 (containing saf5) and pRIT5 (containing the spa gene) (Nilsson et al. (1985) *EMBO J.*, 4:1075-1080) were both digested with restriction enzymes XmaI and PvuI and fragments of approx. size 1.6 kbp and 2.3 kbp were isolated from the respective digests. The isolated fragments were ligated together to yield plasmid pRLM105. This places saf5 downstream from the spa (Staphylococcal Protein A-encoding) gene and maintains the reading frame from the spa gene through saf5.

C. The effect of the Protein A-Saf5 fusion protein on the recrystallization of ice Plasmids pRLM105 (carrying the gene fusion) and pRIT5 (to provide nonfused Protein A for a negative control) were transformed into *E. coli* K12 strain SK1592. Crude extracts from the resultant strains were obtained as in example 1 and tested for recrystallization as in example 3. Ice crystals grew to an average diameter more than five-fold greater in the negative controls compared to the samples containing the fusion protein.

Thus it was shown that the extract containing the Protein A-Saf5 fusion protein inhibited recrystallization, whereas the negative control did not. Example 3 provides data for this fusion protein in pure form.

This demonstrated that a peptide antifreeze attached by its amino-terminus to a foreign heterologous polypeptide can nevertheless function to inhibit recrystallization.

D. Purification of the Protein A-Saf5 fusion Protein

*E. coli* K12 strain SK1592 carrying plasmid pRLM105 was cultured at 37° C. in 100 ml Luria broth (LB) containing 50 μgm/ml ampicillin until it reached an $O.D._{600}$ of approx. 1.0. Cells were pelleted by 5 min. centrifugation at 3000 rpm in an SS34 rotor, and resuspended in 10 ml 30 mM Tris pH 8.1. All subsequent operations were performed at 0°–4° C. After a second centrifugation as before, cells were resuspended in 24 ml of 20% w/v sucrose/30 mM Tris-HCl pH 8.1. 2.4 ml of 1 mg/ml lysozyme in 0.1M EDTA pH 7.3 was added. The cells were then held on ice for 30 min. and subsequently centrifuged for 15 min. at 11,500 rpm in an SS34 rotor. The supernatant was taken and the fusion protein was purified from it by chromatography on IgG-Sepharose.

A column containing 1.5 ml IgG-Sepharose was washed by passage of 20 ml TST (150 mM NaCl, 0.05% Tween 20, 50 mM Tris-HCl pH 7.6). It was then prepared for use by successively passing 4 ml each of (i) 0.5M Acetic Acid pH 3.4, (ii) TST, and (iii) 0.5M Acetic Acid pH 3.4. TST was passed through again until the effluent buffer reached neutral pH. The periplasmic fraction was applied to the column and 15 ml TST and 3 ml 5 mM $CH_3CO_2NH_4$ were subsequently passed through. The Protein A-Saf5 fusion protein was eluted with 20 ml 0.5M Acetic Acid pH 3.4, and the eluted fractions were monitored by absorbance at 280 nm ($A_{280}$=1.0 for approx. 2.6 mg/ml protein); the fractions whose absorbance indicated significant protein content were lyophilized in polypropylene microcentrifuge tubes, and resuspended in 10 mM EDTA/30 mM Tris-HCl pH 8.0 to a final concentration of 0.44 mg/ml. The solution of purified fusion protein was stored at 4 C. This preparation of fusion protein was substantially pure as shown by polyacrylamide gel electrophoresis in the presence of SDS (SDS-PAGE) with subsequent visualization of protein by staining with Coomassie Brilliant Blue.

EXAMPLE 3: Inhibition of recrystallization by purified Protein A-Saf5 fusion protein in water, in popsicle mixture, and in an A&W frozen root beer float mixture A. Inhibition in water The splat assay consists of: 10 μl of the purified Protein A-Saf5 fusion protein (made in example 2D) was added to 90 μl of water and was maintained on ice until used. As a control, 10 μl of a Protein A solution (0.5 mg/ml, in 20 mM Tris-HCl, pH 8.0) was added to 90 μl of water and also maintained on ice until use. A 10 μl droplet of the aqueous sample containing the fusion protein or a 10 μl droplet containing Protein A as the control were released from a height of 3.0 m and allowed to impact upon a polished aluminum plate that was resting upon a block of dry ice (about −75° C.). As the droplet comes in contact with the surface of the cold metal, it instantly freezes and forms a "splat" approximately 10 mm in diameter and 50 μm thick with a composition of very small ice crystals. The splat was then transferred with a cold carbon steel surgical blade (B-P #10) to a glass cryostage mounted on a dissecting microscope.

Photography of recrystallization: In all cases, the sample containing the Protein A-Saf5 fusion protein was splatted first, followed shortly thereafter (within one minute) by the control sample. The splats were then transferred and positioned next to each other on the glass cryostage. The cryostage was connected to a circulating water bath containing 70% ethanol (Neslab exacal model EX-300) which in turn was connected to a flow-through cooler (Neslab model EN-350). The temperature at the point where the splats came in contact with the glass was maintained between −6° to −8° C. The glass cryostage was positioned on the microscope (Zeiss model 47 50 52) between crossed polarizing lenses. The microscope was fitted with a 35mm camera (Zeiss model M35) and the splats were photographed over time using Kodak Tri-X Panchromatic ASA 400 black and white film.

Within the first few minutes following splatting and transfer, both the sample containing the Protein A-Saf5 fusion protein and the control sample containing only Protein A appeared very similar in that they showed a uniform field of very small ice crystals. The splats were maintained under these conditions for at least an hour and were photographed at intervals under magnification. Slide 1—1 of FIG. 7A shows a low magnification (12×) of two splats shortly after freezing and transfer (5 min.). The splat on the right contains the fusion protein mixture at a total protein concentration of 0.1 mg/ml. The control splat on the left contains Protein A alone at a concentration of 0.1 mg/ml. The next three slides show a higher magnification (20×) of recrystallization over time. Slide 1-2 at 15 min., slide 1-3 at 30 min. and slide 1-4 at 1 hour. This Figure shows that after 15 minutes, the splat containing only Protein A (the control) showed a definite increase in the size of the ice crystals while the sample containing the Protein A-Saf5 fusion protein looked much the same as when it was first observed. Photographs were visually inspected to determine average crystal diameters in this and subsequent splat assays. The crystals in the control splat continued to grow over time and after an hour became at least ten times their original diameter while the splat containing the Protein A-Saf5 fusion showed no signs of crystal growth and, in fact, looked much the same as when it was first transferred (see FIG. 7A). Thus the average diameter of the crystals in the negative control became at least ten times that of those in the experimental sample. This demonstrated that a substantially pure fusion protein containing an antifreeze moiety can inhibit recrystallization in frozen water.

B. Inhibition in a popsicle mixture

All experimental conditions were the same as described for example 3A above except that in place of water, the Protein A-Saf5 fusion protein was added to a thawed sample from a popsicle. The sample was an Eskimo (trademark) brand TwinPop (Banana flavored). The ingredients were as follows: Water, sugar, corn sweetener, citric acid, cellulose gum, guar gum, carrageenan, artificial flavors, vitamin C, artificial color, and FD&C yellow #5. This product is distributed by Tomorrow Products, Inc., Los Angeles, Calif. As a control in this experiment, 10 μl of buffer (20 mM Tris-HCl, pH 8.0) was added to the thawed sample in place of 10 μl of the Saf5 fusion protein in the same buffer.

The procedure was to thaw a piece of the confectionery at room temperature, withdraw a small volume, add the SAF fusion protein (or buffer for the control), splat 10 μl samples and photograph recrystallization over time. The additions accounted for 5% of the total volume and the final concentration of the SAF fusion protein mixture was 0.1 mg/ml. The first photographs were taken within 5 minutes after splatting and the remaining pictures show recrystallization at 15 min., 30 min. and one hour. All samples were photographed at the same magnification (20×).

Following splatting and transfer of the samples to the cryostage, they looked very similar in ice crystal size. After an hour of being maintained between −6° to −8° C., it became apparent that the sample to which only buffer had been added was recrystallizing because the average size of the crystals was noticeably larger, whereas the sample to which the Protein A-Saf5 fusion protein had been added did not show any significant crystal growth (see FIG. 7B). This demonstrated that a fusion protein containing an antifreeze moiety can inhibit recrystallization in a commercially available frozen food mixture.

C. Inhibition in an A&W frozen root beer float mixture

All experimental conditions were the same as described for example 3A except that in place of water, the Protein A-Saf5 fusion protein was added to a thawed sample from a frozen A&W (trademark) Root Beer Float Bar. The sample was a composite of a root beer shell with a heart of vanilla ice cream. The ingredients were as follows: Ice cream containing milk fat and non-fat milk, corn sweeteners, sugar and whey, stabilized with guar gum, mono-and diglycerides (with citric acid added as a preservative), food grade xanthin gum and carrageenan, artificially flavored. The root beer shell contains water, sugar, corn syrup, guar gum, caramel color, artificial and natural flavors and sodium benzoate. The product was manufactured by Merritt Foods (plant #29-409), 2840 Guinotte, Kansas City, Mo. As a control, 10 μl of buffer (20 mM Tris-HCl, pH 8.0) was added to the thawed sample in place of 10 μl of the Protein A-Saf5 fusion protein in the same buffer.

The procedure was to thaw a piece of the confectionery at room temperature, withdraw a small volume, add the SAF fusion protein (or buffer for the control), splat 10 μl samples and photograph recrystallization over time. The additions accounted for 5% of the total volume and the final concentration of the SAF fusion protein mixture was 0.1 mg/ml. The first photographs were taken within 5 minutes after splatting and the remaining pictures show recrystallization at 15 min., 30 min. and one hour. All samples were photographed at the same magnification (20×).

The results of splat analysis with this sample were similar to the first two examples in that the control splat showed a definite increase in ice crystal growth after an hour while the sample containing the Protein A-Saf5 fusion protein showed very little ice crystal growth over the same period of time (see FIG. 7C). This demonstrated that a fusion protein containing an antifreeze moiety can inhibit recrystallization in a commercially available ice cream-containing frozen food.

EXAMPLE 4: Inhibition of recrystallization by a Protein A-Saf6 fusion protein

A. Construction of the synthetic antifreeze gene saf6

Two DNA sequences each of 19 bases were synthesized chemically and annealed together to produce the double-stranded oligonucleotide with staggered ends shown as DS oligo 4 (see FIG. 6). Plasmid pGMMl was treated with restriction enzymes AatII and XmaI and the 0.47 kbp fragment of released DNA was separated and purified. In a separate reaction, plasmid pGMMI was also treated separately with restriction enzymes AatII and NheI and the 2.7 kbp fragment of released DNA was separated and purified. These 0.47 kbp and 2.7 kbp fragments were ligated together with DS oligo 4 to yield plasmid pGJ151. This manipulation has the effect of substituting the sequences of DS oligo 4 into the saf3 gene present in pGMM1. The antifreeze-encoding sequences in pGJ151 are known as gene saf6.

B. Construction of the spa-saf6 gene fusion

The spa gene-containing plasmid pRLM101 was used as a vector for saf6. pRLM101 contains the spa gene derived from pRIT5. The construction of pRLM101 is described in this paragraph. Plasmid pGMM1 was treated with restriction enzymes XmaI and PvuI and the 1.75 kbp fragment of released DNA was separated and purified. Plasmid pRIT5 was also treated with XmaI and PvuI and the 2.3 kbp fragment was purified. The purified 1.75 and 2.3 kbp fragments were ligated together to yield plasmid pGMM2. Plasmid pGMM2 was digested by PstI and the 4.2 kbp fragment of released DNA was purified and treated with T4 DNA ligase to yield plasmid pRLM101.

Plasmids pRLM101 and pGJ151 were each treated with restriction enzymes NcoI and PvuI and fragments of approx. size 2.3 kbp and 1.8 kbp were isolated from the respective digests. The isolated fragments were ligated together to yield plasmid pLVC94. This places saf6 downstream from the spa gene and maintains the reading frame from the spa gene through saf6.

C. The effect of the Protein A-Saf6 fusion protein on the recrystallization of ice Plasmid pLVC94 was transformed into E. coli K12 strain JC10291 carrying plasmid pLVC94, and the derivative strain carrying pLVC94 was cultured in 10 ml of LB at 37° C. until an O.D.$_{600}$ of 1.30 was reached. Cells were harvested by centrifugation at 6000 xg for 5 min. and cell extracts were prepared by sonication in 0.5 ml of 10 mM EDTA, 30 mM Tris-HCl pH 8.0 at 4° C. The effect of the Protein A-Saf6 fusion protein present in the cell extracts on recrystallization in water was measured as described for the Betalactamase-Saf3-Betalactamase fusion protein in example 1. Recrystallization was less than in the negative control: crystal size in the control became at least three-fold greater than in the Protein A-Saf6 sample. This demonstrated that Saf6 attached by its amino-terminus to a foreign fusion partner polypeptide can function to inhibit recrystallization.

EXAMPLE 5: Inhibition of recrystallization by a Protein A-Saf8 fusion protein

A. Construction of the synthetic antifreeze gene saf8

Two DNA sequences of 21 and 29 bases respectively were synthesized chemically and annealed together to produce the double-stranded oligonucleotide with staggered ends shown as DS oligo 5 (see FIG. 6). Plasmid pGJ151 was treated with restriction enzymes PstI and AatII and the approx. 0.9 kbp fragment of released DNA was separated and purified. Plasmid pGMMI was treated with restriction enzymes AatII and HindIII and the 2.4 kbp fragment of released DNA was separated and purified. These 0.9 kbp and 2.4 kbp fragments were ligated together with DS oligo 5 to yield plasmid pGMM3. This manipulation has the effect of substituting the sequences of DS oligo 5 into the saf6 gene present in pGJ151. The antifreeze-coding sequences in pGMM3 are known as gene saf8.

B. Construction of the spa-saf8 gene fusion

Plasmids pRLM101 and pGMM3 were each treated with restriction enzymes NcoI and PvuI and fragments of approx. size 2.3 kbp and 1.8 kbp were isolated from the respective digests. The isolated fragments were ligated together to yield plasmid pLVC95. This places saf8 downstream from the spa gene and maintains the reading frame from the spa gene through saf8.

C. The effect of the Protein A-Saf8 fusion protein on the crystallization of ice Plasmid pLVC95 was transferred into *E. coli* K12 strain JC10291 and the derivative strain carrying plasmid pLVC95 was cultured in LB at 37° C. until reaching an $O.D._{600}$ of 1.3. Cells were harvested by centrifugation at 6000 xg for 5 min. and cell extracts were prepared by sonication in 0.5 ml of 10 mM EDTA, 30 mM Tris-HCl pH 8.0 at 4° C. The effect of the Protein A-Saf8 fusion protein present in the cell extracts on recrystallization in water was measured as was done for Betalactamase-Saf3-Betalactamase fusion protein in example 1. The result was that recrystallization was at least sixfold less than in the negative control. This demonstrated that Saf8 attached by its amino-terminus to a foreign polypeptide can function to inhibit recrystallization.

EXAMPLE 6: Purification of two Protein A-Saf10 fusion proteins, inhibition of ice recrystallization by said purified fusion proteins in water, cleavage of one purified fusion protein by CNBr, and activity of naked Saf10 released by said CNBr cleavage A. Construction of the synthetic antifreeze gene saf10

Two DNA sequences of 27 and 33 bases respectively were synthesized chemically and annealed together to produce the double-stranded oligonucleotide with staggered ends shown as DS oligo 6 (see FIG. 6). Plasmid pGMM3 was treated with restriction enzymes EcoRI and NotI such that NotI gave incomplete digestion; DNA fragments of approx. size 81 bp were separated and purified. In a separate reaction, plasmid pGMM3 was also treated with restriction enzymes EcoRI and SacII and the approx. 3.2 kbp fragment of released DNA was separated and purified. These 81 bp and 3.2 kbp fragments were ligated together with DS oligo 6 to yield plasmid pGMM5. This manipulation has the effect of substituting the sequences of DS oligo 6 into the saf8 gene present in pGMM3. The antifreeze-coding sequences in pGMM5 are known as gene saf10.

B. Construction of two spa-saf10 gene fusions

The spa gene-containing vector plasmid pGMM8 was constructed as described in this paragraph. Plasmid pUC118 was cut with PvuII and the 2.9 kbp fragment was ligated to a BglII linker to yield plasmid pGJ153. Plasmid pUC118 was separately cut with EcoRI and HindIII, and the 3.2 kbp fragment of released DNA was ligated together with DS oligo7 to yield plasmid pGJ154. Plasmid pGJ153 was treated with enzymes BglII and AatII and a fragment of 2.1 kbp was isolated. Plasmid pGJ154 was treated with enzymes EcoRI and AatII and a fragment of 0.95 kbp was isolated. Plasmid pRIT2T Nilsson et al. (1985) *EMBO J.* 4:1075–1080) was treated with enzymes BglII and EcoRI and a fragment of 0.9 kbp was isolated. These 2.1, 0.95, and 0.9 kbp fragments were ligated together to yield plasmid pGMM8.

Plasmid pGMM8 was treated with NcoI and BamHI and a fragment of approx. 3.8 kbp was purified. Plasmid pGMM5 was treated with NcoI and BamHI and a fragment of approx. 123 bp was purified. The isolated 3.8 kbp and 123 bp fragments were ligated together to yield plasmid pGMM9, thus placing saf10 downstream from the spa gene, maintaining the reading frame from the spa gene through saf10, and placing a methionine codon at the spa-saf10 junction.

To examine the effect of a different, longer linkage between Protein A and Saf10, a sequence encoding the longer linkage was attached to the upstream end of saf10 to yield plasmid pGMM7, and the combined sequence was then transferred to the spa gene-containing plasmid pGMM8, as follows. Plasmid pGMM5 was treated with EcoRI and NheI, and a fragment of approx. 3.2 kbp was purified. Two DNA sequences each of 34 bases were synthesized chemically and annealed together to produce the double-stranded oligonucleotide with staggered ends shown as DS oligo 8 (FIG. 6). DS oligo 8 was ligated together with the 3.2 kbp fragment to yield plasmid pGMM7. Plasmid pGMM7 was treated with EcoRI and BamHI and the released DNA fragment of approx. 0.15 kbp was purified; plasmid pGMM8 was treated with EcoRI and BamHI and the released DNA fragment of approx. 3.8 kbp was purified. The 0.15 kbp and 3.8 kbp fragments were ligated together to yield plasmid pGMM10. Plasmid pGMM10 contains a spa-saf10 gene fusion equivalent to that in pGMM9 except that the peptide linkage-encoding region supplied by DS oligo 8 is present as the junction between the spa and saf10 moieties.

C. Purification of the Protein A-Saf10 fusion protein

Derivatives of *E. coli* K12 strain N4830 carrying plasmids pGMM9 and pGMM10 respectively were cultured in LB at 28° C. until reaching an $O.D._{600}$ of 1.1. Expression of the spa-saf10 gene fusions was induced by shifting cultures to 42° C. for 90 min. Extracts were obtained as follows: The cell cultures were cooled in ice water and then were pelleted by centrifugation for 10 min. at 2600 xg. Pellets were frozen in liquid nitrogen and stored for future usage. Pellets derived from 100 ml cell cultures were resuspended in 6 ml of 100 mM Tris-HCl pH 8.0 containing 500 mM sucrose, 60 µl 40 mM leupeptin and 400 µl of 100 mM PMSF. To this suspension 120 µl lysozyme of 10 mg/ml were added, mixed briefly and then 6 ml of cold distilled water were added. After incubation at 4° C. for 25 min., 25 µl of DNAse I at 10 mg/ml were added and the cells subjected to eight freeze-thaw cycles in liquid nitrogen and a 37° C. waterbath. The cell lysate was centrifuged for ten minutes at 20,000 xg and the pellet was shown to be free of fusion protein by SDS-PAGE. The supernatant containing the fusion proteins consists mostly of cytoplasmic proteins. The fusion proteins were purified from the extracts as described in example 2 and resuspended in 100 mM NaCl, 50 mM Tris-HCl pH 8.0 to final concentrations of 14 and 8 mg/ml respectively. The solutions of the purified fusion proteins were stored at −20° C. An aliquot was subjected to polyacrylamide gel electrophoresis in the presence of SDS, and the gel was subsequently stained by Coomassie Brilliant Blue. The presence of a single intensely-stained band demonstrated that these preparations of fusion protein were substantially pure.

D. Inhibition of recrystallization by the two purified Protein A-Saf10 fusion proteins The effect of the two purified Protein A-Saf10 fusion proteins on recrystallization in water was measured as for Protein A-Saf5 in example 3. In each case recrystallization was less than in the negative control for both fusion proteins: crystals in the control rapidly exceeded five times the average diameter of crystals in the fusion protein samples. The Protein A-Saf10 fusion protein derived from pGMM10 possessed approx. tenfold more recrystallization-inhibiting activity than that derived from pGMM9, as evidenced by its activity at greater dilution. These observations demonstrated firstly that Saf10 attached to a foreign polypeptide at its amino-terminus can function to inhibit recrystallization, and secondly that certain spacer sequences may be superior to others at the junction between Saf10 and a foreign polypeptide.

E. Release of naked antifreeze peptide Saf10 from the purified Protein A-Saf10 fusion protein A 1 mg quantity of the purified Protein A-Saf10 fusion protein derived from pGMM9 was incubated for approx. 16 hours at 24° C. in the presence of 3.6 $\mu$M cyanogen bromide (CNBr) in 0.1M HCl. The products of the incubation were analyzed by SDS-PAGE and staining by Coomassie Brilliant Blue in parallel with an untreated sample of the purified Protein A-Saf10 fusion protein. This showed that treatment by CNBr resulted in a reduction of concentration of the original protein and the appearance of several proteins smaller than the original protein but larger than 10 kDa. The largest and predominant among these new proteins was one whose size indicated cleavage of the fusion protein at approximately the junction of its Protein A and Saf10 components. Band densities indicated that approximately 80% release of naked antifreeze had occurred, and that cleavage at other sites was less than 50%. On this basis the naked antifreeze was expected to constitute more than 75% of the peptides smaller than 10 kDa but not visible after SDS-PAGE. The protein mixture resulting from CNBr treatment was tested in the recrystallization-inhibition assay described in example 3(A) and was found to retain undiminished ability to retard recrystallization (compared to the untreated fusion protein). The mixture was passed through a molecular filter with a cutoff of 10 kDa. and the filtrate was taken. This 10 kDa. filtrate was expected to contain the "naked" or "free" antifreeze polypeptide (i.e., a polypeptide containing only the indicated polypeptide segments of the SAF) which the CNBr treatment was expected to have generated, but not the residual intact fusion protein or any of the smaller proteins visualized by SDS-PAGE The 10 kDa. filtrate was concentrated by passing it through a molecular filter with a cutoff of 3 kDa. and recovering the retentate. The resulting concentrate of the 10 kDa. filtrate was tested for recrystallization inhibiting activity as before. It was observed to retard recrystallization: the crystals of the negative control rapidly exceeded ten times the average diameter of those in the experimental sample. This demonstrated that a "naked" or "free" antifreeze can be released from a fusion protein, separated from certain other products of the cleavage reaction that produces it while still retaining its recrystallization-inhibiting properties. As evidenced by the visualization of the cleavage products on SDS-PAGE, the naked antifreeze polypeptide was obtained following these procedures in substantially pure form (at least 75% pure).

EXAMPLE 7: Reconstruction experiments with purified Protein A-Saf5 fusion protein and extracts from plant tissue In order to demonstrate that inhibition of recrystallization can occur in plant tissue and that there are no components of the plant cell which are likely to inhibit the activity of the antifreeze protein, reconstruction experiments were carried out where known amounts of the Protein A-Saf5 fusion protein (made in example 2D) were added to cell-free extracts from plant tissue. The extracts were made by freezing a small (ca.8 cm in length) leaf of the tobacco cultivar SR1 in liquid nitrogen and grinding it to a fine powder in a cooled mortar and pestle. The powder was then transferred to a capped polycarbonate tube and mixed by vortexing for 20 seconds with 2 ml of extraction buffer (50 mM NaH-$PO_4$ pH 7.0, 10 mM DTT, 0.1% TRITON X-100, 1 mM $Na_2EDTA$). The tube was then spun at 2700 rpm in a Beckman TJ-6 centrifuge to pellet debris. 1 ml of the supernatant from this spin was spun for 5 minutes in an Eppendorf centrifuge. The clear supernatant was taken and the protein concentration determined using the protein assay kit from Bio-Rad.

The Protein A-Saf5 fusion protein was added to the plant extract and the resulting mixture was assayed for recrystallization inhibition as described in example 3. The plant extract containing only buffer (the negative control) showed an increase in the diameter of the crystals that was at least five times greater than the plant extract sample containing the Protein A-Saf5 fusion protein. The results of this experiment demonstrated recrystallization inhibition when the Protein A-Saf5 fusion protein represented 0.1% of the total protein by mass.

EXAMPLE 8: Plant transformation with saf10

A. Construction of plasmids for expression of antifreeze proteins in transgenic plants In order to obtain expression of the antifreeze protein in plants, the antifreeze gene saf10 (described in example 6A) was cloned into plasmids which were suitable for plant transformation by the method of co-cultivation with *Agrobacterium tumefaciens*. The vectors were constructed in such a way that the antifreeze gene would be expressed in plants under the control of the 35S promoter which is derived from the cauliflower mosaic virus and which is known to give high levels of expression of foreign genes in plant cells. Additional features of these vectors were the possession of a leader sequence derived from the petunia Cab22L gene, which is known to further enhance expression in plants, and a 3' polyadenylation sequence derived from the *Agrobacterium tumefaciens* nopaline synthase gene, which is known to permit efficient post-transcriptional processing of messenger RNAs of which it is a part. In addition, some of the vectors contained DNA sequences derived from bacterial or plant genes for secreted proteins, in order to produce antifreeze polypeptides which would be secreted from the plant cell.

B. Plasmids used in the construction of saf10 derivatives

The plasmid p35S(J):Cab22L-CH contains the CaMV 35S promoter followed by the leader sequence derived from the Cab22L gene of petunia. Downstream of these sequences is the bacterial chiA (chitinase A) gene, which has been modified to have a unique NcoI site at the ATG start codon. Beyond the end of the coding sequence for the bacterial chiA gene is a unique BamHI site, followed by the nos (nopaline synthase) polyadenylation signal. Beyond this is a unique HindIII site. The backbone of this plasmid is the vector pUC118, which is commercially available. Thus it is possible to prepare this plasmid in either single or double stranded form. The construction of this plasmid has been published (M. H. Harpster et al. (1988) Mol. Gen. Genet., 212:182–190).

The plasmid pCHIT-503 was derived from the plasmid p35S(J):Cab22L-CH, by introducing a SmaI site by site directed mutagenesis at a position immediately downstream of the codons for the chiA signal sequence. The method of site directed mutagenesis used has been described (T. A. Kunkel, (1985) Proc. Natl. Acad. Sci. USA, 82:488–492). In order to do this the oligonucleotide 5'-TTGCCCGGGGCGGCG-3', which is complementary to the chiA sequence from positions +69 to +83 with a single base pair change at position +75 which creates a SmaI site without changing any of the amino acids in the translated protein, was annealed to single stranded p35S(J):Cab22L-CH which had been prepared from the E. coli strain BW313. The oligonucleotide was extended in the presence of all four deoxyribonucleotide triphosphates and the Klenow fragment of DNA polymerase I and T4 DNA ligase. The polymerase extended and ligated plasmids were transformed into E. coli HB101. Individual transformants were picked and plasmid DNA from each was screened for the presence of the new SmaI site. One such transformant was found which had the correct restriction digest pattern, and this was named pCHIT503.

The plasmid pCHIT503-21 was derived from the plasmid pCHIT503 by removing a SmaI site present in the wild-type chiA gene using site-directed mutagenesis. This was done so that the newly introduced SmaI site would be the only SmaI site in the plasmid. In order to do this the oligonucleotide 5'-CTTTGCCGCCAGGGAACTCC-3' (which is complementary to the chiA sequence from positions +942 to +961 with a single base pair change at position +951 and which destroys the SmaI site but does not change any amino-acids in the ChiA protein) was annealed to single stranded pCHIT503 which had been prepared from the E. coli strain BW313. The oligonucleotide was extended in the presence of all four deoxyribonucleotide triphosphates and the Klenow fragment of DNA polymerase I and T4 DNA ligase. The polymerase extended and ligated plasmids were transformed into E. coli HB101. Individual transformants were picked and plasmid DNA from each was screened for the loss of the SmaI site. One such transformant was found which had the correct restriction digest pattern, and this was named pCHIT503-21.

The plasmid pCHIT500 contains the codons for the tobacco PR1b signal sequence synthesized as two oligonucleotides and cloned as an NcoI-SmaI fragment in the plasmid pUC118. The oligonucleotides were designed so that when annealed and cloned into pUC118, they would have a SmaI site at the 3' end, which if used to clone the PR1b signal sequence fragment into pCHIT503-21 would put the codons for the PR1b signal sequence in the same reading frame as the codons for the ChiA protein. The oligonucleotides were: 5'-CATGGGATTT TTTCTCTTTT CACAAATGCC CTCATTTTTT CTTGTCTCTA CACTTCTCTT ATTCCTAATA ATATCTCACT CTTCTCATGC CCAAAACCC-3' and 5'-GGGTTTTGGG CATGAGAAGA GTGAGATATT ATTAGGAATA AGAGAAGTGT AGAGACAAGA AAAAATGAGG GCATTTGTGA AAAGAGTAAA AATCCC-3'. The PR1b protein is a protein whose synthesis is induced by pathogen attack. It is a secreted protein and possesses a signal sequence (J. P. Carr et al. (1987) Mol. Cell Biol., 7:1580–1583; B. J. C. Cornelissen et al. (1986) EMBO J., 5:37–40).

The plasmid pCHIT-PRSS was derived from the plasmid pCHIT503-21 by replacing the NcoI-SmaI fragment from pCHIT503-21 (which carries the codons for the ChiA signal sequence) with the NcoI-SmaI fragment pCHIT500 which carries the signal sequence of the PR1b protein from tobacco. To do this, pCHIT503-21 DNA was cut with the restriction enzymes NcoI and SmaI. pCHIT500 was cut with NcoI and SmaI and the smaller fragment released was purified from a polyacrylamide gel. The small fragment was ligated with the NcoI-SmaI cut pCHIT503-21 with a large molar excess of the smaller fragment, and transformed into the E. coli strain MV1193. DNA was prepared from some of the transformants, and the desired plasmid was identified by restriction enzyme analysis. The plasmid which carries the PR1b signal sequence fused in frame to the chiA coding sequence was designated pCHIT-PRSS.

The plasmid pCHIT-PRSS2 was derived from the plasmid pCHITPR-SS by site directed mutagenesis, after it was discovered by DNA sequence analysis that the PR1b signal sequence cloned in the plasmid pCHIT-PRSS carried a single base pair change which would lead to an amino-acid substitution in the PR1b signal sequence. This was a change from T to A at position 12 of the PR1b sequence, which changes a codon for leucine (the wild type sequence) to a codon for phenylalanine. As it was not known what effect this mutation would have on the ability of the PR1b signal sequence to mediate the secretion of the protein to which it was translationally fused, this mutation was corrected back to the wild type, using the same site directed mutagenesis protocol as described above. The oligonucleotide which had been synthesized in order to produce the plasmid pCHIT500 and which coded for the top strand of the PR1b gene was used for the mutagenesis. The correct plasmid was identified by DNA sequence analysis, and was designated pCHIT-PRSS2. The only difference between the two plasmids pCHIT-PRSS and pCHIT-PRSS2 is the single base pair difference in the region of the plasmid coding for the PR1b signal sequence.

The construction of pCHIT503, pCHIT503-21, pCHIT-PRSS and pCHIT-PRSS2 is summarized in FIG. 8A.

The plasmid pJJ2964 is a plasmid which has been specifically designed for plant transformation by Agrobacterium tumefaciens. It contains sequences permitting it to replicate both in E. coli and Agrobacterium tumefaciens, and a gene encoding resistance to tetracycline which enables it to be selected for in both these bacteria. It contains the left border and right border sequences of T-DNA which are required for efficient transfer to plant cells and integration into the plant's DNA. Between these borders, it contains the gene encoding resistance to kanamycin under the control of the nos promoter and with the polyadenylation signal from the octopine synthase gene, so that plant cells which have become transformed can be detected by their ability to grow on this antibiotic. It is derived from the vector pRK290. It also contains unique BamHI and HindIII sites between the left border and right border of the T-DNA, such that any sequence which is cloned between these two sites will be efficiently transferred and integrated into plant DNA. This plasmid was constructed as follows. The broad host range plasmid pRK290 (G. Ditta et al. (1980) *Proc. Natl. Acad. Sci. USA*, 77:7347-7351) was cut with the restriction enzyme EcoRI, and the overhanging ends were filled in with the Klenow fragment of DNA polymerase I plus the four deoxyribonucleotide triphosphates. The plasmid pAGS111 (P. van den Elzen et al. (1985) *Plant Mol. Biol.*, 5:149-154) was cut with the restriction enzymes HindIII and EcoRI, and the overhanging ends were filled in with the Klenow fragment of DNA polymerase I plus the four deoxyribonucleotide triphosphates. The two cleaved DNAs were ligated and transformed into *E. coli*. A plasmid was identified by restriction enzyme analysis that contained the EcoRI-HindIII fragment from pAGS111 containing the nptII gene from pAGS111, and the right and left borders of the T-DNA (which are essential for transfer and integration of DNA from Agrobacterium to plant cells) inserted into the EcoRI site in pRK290. This plasmid was designated pJJ1881. pJJ1881 was cut with ClaI and BamHI and ligated with pBR322 (a commercially available plasmid) which had been cut with ClaI and BamHI, and the ligation product was transformed into *E. coli*. A plasmid was identified where the ClaI-BamHI fragment from pJJ1881 carrying the nptII gene had been replaced with the small ClaI-BamHI fragment from pBR322, which has a HindIII site downstream of the ClaI site. This plasmid was designated pJJ2431. The plasmid pLGVNeo2103 (van den Elzen et al., 1985) was cut with EcoRI, treated with S1 nuclease to remove single stranded DNA, and ligated with ClaI linkers. The ligation was cut with ClaI and the plasmid purified away from the linkers, then religated and transformed into *E. coli*. A plasmid was identified where the EcoRI site in pLGVNeo2103 had been converted to a ClaI site, and this plasmid was designated pAGS109. pAGS109 was cut with ClaI and HindIII, and ligated with pJJ2341 which had been cut with ClaI and HindIII. A plasmid which contained the nptII gene in the backbone derived from pJJ2341 was identified and designated pJJ2964. The construction of pJJ2964 is shown in FIG. 8B.

C. Construction of plasmids for expression of an antifreeze gene in plants

In order to construct a vector where the antifreeze gene saf10 was situated downstream of the CaMV 35S promoter and the Cab22L leader, and with the nos polyadenylation signal at its 3' end, 10 µg of pGMM5 was digested with the restriction endonucleases NcoI and BamHI. The products of the digestion were electrophoresed on a 9% polyacrylamide gel, and a fragment of the expected size (127 base-pairs) was seen. This band was excised from the gel and electroeluted. The DNA was recovered by extracting once with an equal volume of 1:1 phenol and chloroform saturated with TE (10 mM TRIS pH 8.0, 1 mM EDTA), followed by precipitation with 0.3M NaOAc, 10 µg of yeast tRNA and 2.5× volumes of ethanol. The purified DNA fragment was resuspended in 20 µl TE. 2 µg of pCHIT503-21 was cut with the restriction endonucleases NcoI and BamHI, and electrophoresed on a 0.8% agarose gel. The vector backbone fragment was electroeluted and resuspended in 20 µl TE. To ligate the NcoI-BamHI fragment containing the saf10 gene into the NcoI-BamHI backbone from pCHIT503-21, 10 µl of the purified fragment was mixed with 1 µl of the purified backbone, in a final volume of 20 µl ligase buffer (50 mM NaCl, 100 mM TRIS pH 7.5, 10 mM MgCl$_2$, 1 mM dithiothreitol, 1 mM ATP, 1 unit T$_4$ DNA ligase) and incubated overnight at 4° C. This buffer is hereafter referred to as "ligase buffer". The following day the ligation products were transformed into competent cells of *E. coli* strain MV1193, and transformants were selected by growth on LB agar containing 75 µg/ml ampicillin. To verify the presence of the correct plasmid in the transformed colonies, DNA was prepared from individual colonies and cleaved with the restriction endonucleases XhoI and HindIII. The predicted size fragments (447 base-pairs) were observed following gel electrophoresis in 0.8% agarose. The correct plasmid was named pCHIT-AFNB.

In order to be able to express a form of the antifreeze protein that would be secreted from plant cells, the antifreeze gene was first fused in the correct reading frame to a signal sequence from the bacterial chitinase gene chiA or the tobacco pathogenesis related protein PR1b, as follows. 10 µg of pGMM5 was digested with the restriction endonucleases SmaI and BamHI. The products of the digestion were electrophoresed on a 9% polyacrylamide gel, and a fragment of the expected size (133 base-pairs) was seen. This band was excised from the gel and electroeluted. The DNA was recovered by extracting the buffer once with an equal volume of 1:1 phenol and chloroform saturated with TE, followed by precipitation with 0.3M NaOAc, 10 µg of yeast tRNA and 2.5× volumes of ethanol. The purified DNA fragment was resuspended in 20 µl TE. 2 µg of pCHIT503-21 was cut with the restriction endonucleases SmaI and BamHI, and electrophoresed on a 0.8% agarose gel. This cleavage produced two fragments: the fragment containing the coding region for the mature part of the chitinase protein (i.e., that part of the protein which is left after cleavage of the signal sequence) and the backbone of the vector containing the selectable ampicillin resistance marker, the sequences required for plasmid replication, the CaMV 35S promoter, the Cab22L leader, the codons for the ChiA signal sequence (terminating in a SmaI site), and the nos polyadenylation signal (starting with a BamHI site). The vector backbone fragment was electroeluted and resuspended in 20 µl TE. To ligate the SmaI-BamHI fragment containing the saf10 gene into the SmaI-BamHI backbone from pCHIT503-21, 10 µl of the purified fragment was mixed with 1 µl of the purified backbone, in a final volume of 20 µl ligase buffer and incubated overnight at 4° C. The following day the ligation mix was transformed into competent cells of the *E. coli* strain MV1193, and transformants were selected by growth on LB agar containing 75 µg/ml ampicillin. To verify the presence of the correct plasmid in the transformed colonies, DNA was prepared from individual colonies and cleaved with the restriction endonucleases XhoI and HindIII. The predicted size fragment (530 base-pairs) was observed following gel electrophoresis in 0.8% agarose. A second cleavage with NcoI was then carried out to confirm that the correct ligation product had been recovered. The predicted fragment of 83 base-pairs was seen following electrophoresis in 8% polyacrylamide. The correct plasmid was named pCHIT-AFSB.

A vector was constructed where the antifreeze gene saf10 was fused in frame to the signal sequence from the tobacco PR1b gene, situated downstream from the CaMV 35S promoter with the Cab22L leader, and with the nos polyadenylation signal at the 3' end. The procedure was identical to that described in the previous paragraph, except that the SmaI-BamHI fragment de- being shown from the initiating ATG to the HindIII site:

Antifreeze gene (saf10) following cloning of NcoI-BamHI into NcoI-BamHI cut pCHIT503.
length: 130

| | | | | |
|---|---|---|---|---|
| 1 ATGGACACTG | CTAGCBATGC | CGCCGCGGCC | GCTGCTTTGA | CAGCTGCTAA |
| 51 CGCCGCCGCG | GCCGCTAAAC | TGACTGCAGA | TAATGCTGCC | GCGGCAGCAG |
| 101 CAGCAACTGC | ACGTTAACAA | CATCCGGATC | | |

Antifreeze gene (saf10) fused in frame to chiA signal sequence.
length: 221

| | | | | |
|---|---|---|---|---|
| 1 ATGGCCAAAT | TTAATAAACC | GCTGTTGGCG | CTGTTGATCG | GCAGCACGCT |
| 51 GTGTTCCGCG | GCGCAGGCCG | CCGCCCCGGG | TACCATGGAC | ACTGCTAGCG |
| 101 ATGCCGCCGC | GGCCGCTGCT | TTGACAGCTG | CTAACGCCGC | CGCGGCGTTA |
| 151 AAACTGACTG | CAGATAATGC | TGCCGCGGCA | GCAGCAGCAA | CTGCACGTTA |
| 201 ACAACATCCG | GATCCAAGCT | T | | |

Antifreeze gene saf10, cloned as pAFSS (with PR1b signal sequence containing the mutation at position 12)
length: 242

| | | | | |
|---|---|---|---|---|
| 1 ATGGGATTTT | TACTCTTTTC | ACAAATGCCC | TCATTTTTTC | TTGTCTCTAC |
| 51 ACTTCTCTTA | TTCCTAATAA | TATCTCACTC | TTCTCATGCC | CAAAACCCGG |
| 101 GTACCATGGA | CACTGCTAGC | GATGCCGCCG | CGGCCGCTGC | TTTGACAGCT |
| 151 GCTAACGCCG | CCGCGGCCGC | TAAACTGACT | GCAGATAATG | CTGCCGCGGC |
| 201 AGCAGCABCA | ACTBCACGTT | AACAACATCC | GGATCCAAGC | TT |

Antifreeze gene saf10, cloned as pAFSS2
length: 242

| | | | | |
|---|---|---|---|---|
| 1 ATGGGATTTT | TTCTCTTTTC | ACAAATGCCC | TCATTTTTTC | TTGTCTCTAC |
| 51 ACTTCTCTTA | TTCCTAATAA | TATCTCACTC | TTCTCATGCC | CAAAACCCGG |
| 101 GTACCATGGA | CACTGCTAGC | GATGCCGCCG | CGGCCGCTGC | TTTGACAGCT |
| 151 GCTAACGCCG | CCGCGGCCGC | TAAACTGACT | GCAGATAATG | CTGCCGCGGC |
| 201 AGCAGCAGCA | ACTGCACGTT | AACAACATCC | GGATCCAAGC | TT | rived from pGMM5 was cloned in to SmaI-BamHI cleaved pCHIT-PRSS2. The correct plasmid was identified by restriction analysis of plasmid DNA from the transformants produced from this ligation. Digestion with XhoI and HindIII released a fragment of size 551 base-pairs, and cleavage with NcoI produced a fragment of 104 base-pairs. The desired plasmid was named pCHIT-AFSS2.

A vector was constructed where the antifreeze gene saf10 was fused in frame to the mutated signal sequence from the tobacco PR1b gene, and situated downstream from the CaMV 35S promoter with the Cab22L leader, and with the nos polyadenylation signal at the 3' end. The procedure was identical to that described in the previous paragraph, except that the SmaI-BamHI fragment derived from pGMM5 was cloned in to SmaI-BamHI cleaved pCHIT-PRSS. The correct plasmid was identified following cleavage of plasmid DNA from the transformants produced from this ligation with XhoI and HindIII which released a fragment of size 551 base-pairs. The desired plasmid was named pCHIT-AFSS.

The sequences of the antifreeze genes in the plasmids pCHIT-AFNB, pCHIT-AFSB, pCHIT-AFSS, and pCHIT-AFSS2, are as followed, with the sequence The predicted amino acid sequences of the proteins produced by translation of the above DNA sequences are as follows:

Antifreeze gene (saf10) following cloning of NcoI-BamHI into NcoI-BamHI cut pCHIT503.
1    MDTASDAAAA AALTAANAAA AAKLTADNAA AAAAATAR*
Antifreeze gene (saf10) fused in frame to chiA signal sequence.
1    MAKFNKPLLA LLIGSTLCSA AQAAAPGTMD TASDAAAAAA LTAANAAAAA
51   KLTADNAAAA AAATAR*
Antifreeze gene saf10, cloned as pAFSS (with PR1b signal sequence containing the mutation at position 12)
1    MGFLLFSQMP SFFLVSTLLL FLIISHSSHA QNPGTMDTAS DAAAAAALTA
51   ANAAAAAKLT ADNAAAAAAA TAR*
Antifreeze gene saf10, cloned as pAFSS2
1    MGFFLFSQMP SFFLVSTLLL FLIISHSSHA QNPGTMDTAS DAAAAAALTA
51   ANAAAAAKLT ADNAAAAAAA TAR*

The entire sequences containing the CaMV 35S promoter, the Cab22L leader, the chiA or PR1b signal sequences if present, the antifreeze gene and the nos polyadenylation signal were transferred into a vector which could be used to transform plant cells. 20 μg of purified pCHIT-AFNB, pCHIT-AFSB, pCHIT-AFSS or pCHIT-AFSS2 were cut with BglII and HindIII. BglII cuts in the region of DNA 5' to the CaMV 35S promoter, and HindIII cuts in the region of DNA 3' to the nos polyadenylation sequence. The BglII-HindIII fragments were purified by electroelution from a 0.8% agarose gel, extracted with a 1:1 mixture of phenol and chloroform and precipitated with 0.3M NaOAc, yeast tRNA and ethanol as described above. The purified fragments were resuspended in 25 μl TE. Each fragment was then cloned into the binary vector pJJ2964. 10 μg of pJJ2964 DNA was cut with the restriction endonucleases BamHI and HindIII, purified from a 0.8% agarose gel by electroelution, phenol/chloroform extracted, and ethanol precipitated, as described above. The cut DNA was resuspended in 20 μl TE. To ligate the antifreeze expression cassette into the binary vector, 2 μl of the purified BamHI-HindIII cut binary vector was mixed in separate reactions with 2 μl of each of the purified BglII-HindIII fragments and the mixtures were incubated overnight at 4° C. in a final volume of 20 μl ligase buffer. The ligations were then transformed into competent cells of *E. coli* HB101 and plated on LB medium containing 10 μg/ml tetracycline. Plasmid DNA was prepared from colonies that grew on these plates and cut with the enzymes XhoI and HindIII. The cleaved plasmid DNA was checked by electrophoresis on a 1% agarose gel for the presence of the correct sized fragment. Fragments of the predicted size were seen in each case, confirming that the correct ligation product had been obtained. The plasmids obtained were named 2964-AFNB, 2964-AFSB, 2964-AFSS and 2964-AFSS2. These were derived from pCHIT-ASNB, pCHIT-AFSB, pCHIT-AFSS and pCHIT-AFSS2, respectively. Details of these constructions are shown in FIG. 8C.

D. Transformation of tobacco with binary plasmids containing antifreeze genes i) Introduction of the binary plasmids into Agrobacterium tumefaciens Prior to transformation of plant tissue, the binary asmids derived from pJJ2964 were introduced into *A. tumefaciens* strain LBA4404 by triparental mating. Fresh cultures of *A. tumefaciens* LBA4404 harboring plasmid pAL4404 were grown at 28° C. for 24 h from a single colony in minimal A (10.5 g $K_2PO_4$, 4.5 g $KH_2PO_4$, 1 g $(NH_4)_2SO_4$, 0.5 g NaCitrate.$2H_2O$), 1 ml 1M $MgSO_4.7H_2O$, 10 ml 20% glucose, water to 1 l). *E. coli* HB101 containing the plasmid pRK2013 and *E. coli* HB101 containing the pJJ2964 derivatives described above were grown for 6 hours in L broth. 0.5 ml of the *A. tumefaciens* culture was mixed on the same LB agar plate with 0.25 ml of HB101/pRK2013 and 0.25 ml of HB101 containing one of the pJJ2964 derivatives, and the plates were incubated for 24 hours at 28° C. A loopful of bacteria from each plate was then resuspended in 1 ml minimal A and plated at $10^0$, $10^{-2}$ and $10^{-4}$ dilutions on LB plates containing 100 μg/ml rifampicin and 100 μg/ml tetracycline. After several days growth at 28° C., individual colonies were restreaked onto minimal A plates containing 1 μg/ml tetracycline.

ii) Transformation of tobacco

All manipulations were carried out under sterile conditions. A culture of the Agrobacterium strain containing the requisite binary plasmid was grown for 24 hours in minimal A medium at 28° C. Leaf discs were punched from the leaves of sterilely grown SRI *Nicotiana tabacum* plants using a cork borer with internal diameter 0.5 cm. The Agrobacterium cultures were diluted in MS/B5 0.1/1.0 (defined below) to a final concentration of $5 \times 10^5$/ml. MS/B5 0.1/1.0 was prepared as follows: A 10× stock of MS major salts was prepared, containing (per liter) 16.5 g $NH_4NO_3$, 19 g $KNO_3$, 3.7 g $MgSO_4.7H_2O$, 1.7 g $KH_2PO_4$, 4.4 g $CaCl_2.2H_2O$. A 1000× stock of MS minor salts was prepared containing (per liter) 19800 mg $MnCl_2.4H_2O$, 6200 mg $H_3BO_3$, 8625 mg $ZnSO_4.7H_2O$, 830 mg KI, 250 mg $NaMoO_4.2H_2O$; 25 mg $CuSO_4.5H_2O$, 25 mg $CoCl_2.6H_2O$. A 100× stock of B5 vitamins was prepared containing per liter 100 mg nicotinic acid, 1000 mg thiamine HCl, 100 mg pyridoxine HCl, 10000 mg myo-inositol. A 100× stock of MS FeEDTA was prepared containing per liter 3.73 g $Na_2EDTA$, 2.78 g $FeSO_4.7H_2O$. MS/B5 0.1/1.0 was made up as follows:

| Ingredient | Stock | Amount/liter |
|---|---|---|
| MS major salts | 10x | 100 ml |
| MS minor salts | 1000x | 1 ml |
| MS FeEDTA | 100x | 10 ml |
| B5 vitamins | 100x | 10 ml |
| MES | | 0.59 g |
| Sucrose | | 30 g |
| Naphthalene acetic acid | | 0.1 mg |
| 6-benzylaminopyrine | | 1.0 mg |

For solid MS/B5 0.1/1.0, 8 g agar was added per liter. The leaf discs were dipped into the Agrobacterium suspension for 1 second each and then placed on co-cultivation plates, with 10 discs per plate. Co-cultivation plates are solid MS/B5 0.1/1.0 overlaid with a single, sterile Whatman #1 7 cm filter disc. The leaf discs were co-cultivated with the Agrobacterium for 2 days at 28° C. The co-cultivation was terminated by washing the leaf discs in MS/B5 0.1/1.0 containing 500 μg/ml cefotaxime for 6 hours with one change of medium. The discs were then placed on solid MS/B5 0.1/1.0 containing 500 μg/ml cefotaxime and incubated for 3 days at 28° C. The discs were then transferred to selective medium: MS/B5 0.1/1.0 containing 500 μg/ml cefotaxime and 100 μg/ml kanamycin. The discs were cultured on this medium under high light fluence with a 16 hour light, 8 hour dark regime at 26° C. After 2-3 weeks, kanamycin resistant callus and subsequently kanamycin resistant shoots begin to appear. When these were sufficiently large to handle with sterile forceps, they were transferred to rooting medium (MS 0.1/1.0 with no naphthalene acetic acid or 6-benzylaminopurine, containing 2 μM indole butyric acid) without selection, and allowed to form roots for 14 days. They were then excised and retransferred to rooting medium containing 100 μg/ml kanamycin. Plants that successfully developed roots on this medium were all transformants. They were then transferred to Magenta boxes containing solid MS 0.1/1.0 without naphthalene acetic acid or 6-benzyl aminopyrine.

E. Assay of expression of an antifreeze gene in transformed tobacco

To assay for the levels of expression of the introduced antifreeze gene, RNA was extracted from leaves of transformed plants and assayed for the presence of the antifreeze mRNA by using the technique of RNase protection.

RNA was extracted from leaves of six in vitro grown tobacco plants, each one of which was the product of a unique transformation event with the binary plasmid 2964-AFNB. Two leaves 3-4 cm long were taken from each plant, frozen in liquid nitrogen, and ground to fine powder using a mortar and pestle. The powder was transferred to a capped polypropylene tube containing 5 ml phenol (equilibrated with water), 5 ml chloroform, and 5 ml NTES (0.1M NaCl, 0.01M TRIS HCl pH 7.5, 1 mM EDTA, 1% SDS) and the tube was vortexed for 30 seconds. The extraction mix was then transferred to a 30 ml Corex tube and spun at 8,000 rpm for 10 min. in a Sorvall SS-34 rotor. The upper aqueous layer was removed, and the extraction was repeated until the aqueous layer was clear and there was no precipitation material at the interface between the organic and the aqueous layers. The aqueous layer was then transferred to a fresh 30 ml Corex tube containing 0.5 ml 3M NaOAc pH 6, and 12.5 ml ethanol was added. The contents of the tube were mixed and then chilled to −20° C. for 20 minutes. The tube was then spun at 8,000 rpm for 15 minutes in a Sorvall SS-34 rotor, to pellet the nucleic acid. The pellet was resuspended in 2.5 ml 4M LiOAc, and incubated at 4° C. for 3 hours. The tube was then spun at 8,000 rpm for 15 min. in an SS-34 rotor to pellet the RNA. The pellet was resuspended in 2.5 ml water, to which was added 250 µl 3M NaOAc pH 6 and 7 ml ethanol. The tube was spun again at 8,000 rpm for 15 min. and the pellet was washed with 5 ml 70% ethanol. The pellet was dried under vacuum, and then resuspended in 200 µl water.

To establish the presence of the expected mRNA in the RNA extracted from the transformed plants, the technique of RNase protection was used. In this technique, a short probe which is complementary to the expected message is synthesized such that it is labelled with $^{32}P$. It is then hybridized with the plant RNA. After hybridization has occurred, the RNA is digested with enzymes which are specific for single stranded RNA. If sequences complementary to the probe are present in the RNA preparation, they will anneal with the probe to form a double-stranded RNA which will be resistant to RNase digestion. This can then be detected by gel electrophoresis and autoradiography.

To make a probe that would detect the antifreeze gene, the EcoRI-HindIII fragment was cloned from pGMM5 into the commercially available plasmid Bluescript(−), at the EcoRI and HindIII sites. The resulting plasmid is referred to as BS(−)AF. BS(−)AF DNA was purified and 5 µg was digested with EcoRI, which cuts upstream of the ATG of the antifreeze gene. The cut DNA was purified by extraction with phenol and chloroform and precipitated with 0.3M NaOAc and ethanol. $^{32}P$-labeled RNA complementary to the antifreeze message was synthesized by using the riboprobe reaction as described in the commercial literature from Promega Biotech Inc. using T3 RNA polymerase. The purified labeled probe was resuspended in 25 µl water. 10 µg RNA from each one of the six transformed plants, and 10 µg RNA from a tobacco plant transformed with a different binary vector not containing the antifreeze gene, was dried under vacuum, and then resuspended in 30 µl hybridization buffer (40 mM PIPES (ph 6.7), 0.4M NaCl, 1 mM EDTA). A control tube was also made which contained 10 µg tRNA from yeast. 1 µl of probe was added to each sample. The samples were overlaid with 30 µl mineral oil to prevent evaporation, incubated at 85° C. for 5 min., then at 45° C. for 18 hours. Digestion with RNase A and T1 RNase and preparation of the samples for loading onto a denaturing 6% polyacrylamide gel was then carried out as described in the commercial protocol from Promega Biotech Inc. Also loaded on the same gel were size markers (pBR322 DNA cleaved with HpaII and labeled with $^{32}P$) and a 500× dilution of the original riboprobe.

Following electrophoresis, the gel was fixed for 10 min. in 10% acetic acid, 10% methanol, then dried onto Whatman filter paper No. 1, and autoradiographed, see FIG. 9.

From comparing the sequence of the antifreeze gene in the plasmid pGMM5 with the sequence of the antifreeze gene as cloned in the plasmid 2964-AFNB, it can be predicted that, if an mRNA corresponding to the antifreeze gene is indeed being synthesized in the transgenic plants, the RNase protection assay described above should lead to a protected fragment of 134 base pairs. A fragment of this size was seen in the lanes containing RNA from each of the transformed plans, but not in the control lanes from the plant not expressing the antifreeze gene, or from the control lane with tRNA only. The relative intensities of the bands varied, reflecting the known fact that the level of expression of any introduced gene varies between individual regenerated plants from the same transformation experiment. The results of this experiment showed that a synthetic gene for the antifreeze protein can be introduced into plants, and that this gene is expressed in the plant tissue.

Although the present invention has been described in some detail by way of illustration and example for purposes of clarity of understanding, it will be apparent that certain changes and modifications may be practiced within the scope of the claims.

We claim:

1. A fusion protein consisting essentially of a polypeptide exhibiting ice crystal growth suppression activity and a heterologous protein domain selected from the group consisting of Protein A and β-lactamase, wherein the polypeptide has the formula:

X1-X2-X3, and is selected from the group consisting of:
 Saf3 wherein X1 is MAA; X2 is type 1-type 3-type 3 and X3 is ATAA;
 Saf5 wherein X1 is MAA; X2 is type1-type3-type3-type3-type3 and X3 is ATAA;
 Saf6 wherein X1 is M; X2 is type1-type3-type3 and X3 is ATAA;
 Saf8 wherein X1 is M; and X2 is type1-type3—type3 and X3 is ATAR; and
 Saf10 wherein X1 is M; X2 is type1-type4-type5 and X3 is ATAR;
and wherein:
 type1 is DTASD AAAAAA,
 type2 is LTAAN AKAAAE,
 type3 is LTAAN AAAAAA,
 type4 is LTAAN AAAAAK,
 type5 is LTADN AAAAAA,
 type6 is ATAAT AAAAAA, and
 type7 is ATAAT AAKAAA.

2. A fusion protein according to claim 1, wherein the fusion protein is β-lactamase-Saf3-β-lactamase.

3. A fusion protein according to claim 1, wherein the fusion protein is Protein A-Saf5.

4. A fusion protein according to claim 1, wherein the fusion protein is Saf6-Protein A.

5. A fusion protein according to claim 1, wherein the fusion protein is Saf8-Protein A.

6. A fusion protein according to claim 1, wherein the fusion protein is Protein A-Met-Saf10.

7. A fusion protein according to claim 1, wherein the fusion protein is Protein A-Arg-Val-Asp-Ile-Glu-Gly-Arg-Saf10.

* * * * *